United States Patent
Munoz et al.

(10) Patent No.: US 6,231,187 B1
(45) Date of Patent: May 15, 2001

(54) METHOD AND APPARATUS FOR DETECTING EYE MOVEMENT

(75) Inventors: Douglas P. Munoz, Kingston (CA); Gerald E. Loeb, South Pasadena, CA (US); Karen A. Hampton; Martin W. Ten Hove, both of Kingston (CA)

(73) Assignee: Queen's University at Kingston, Kingston (CA)

( * ) Notice: Subject to any disclaimer, the term of this patent is extended or adjusted under 35 U.S.C. 154(b) by 0 days.

(21) Appl. No.: 09/501,190

(22) Filed: Feb. 10, 2000

Related U.S. Application Data

(60) Provisional application No. 60/119,641, filed on Feb. 11, 1999.

(51) Int. Cl.[7] .................................................. A61B 3/14
(52) U.S. Cl. ........................................... 351/209; 600/558
(58) Field of Search ..................................... 351/202, 203, 351/205, 209, 210; 600/544, 545, 554, 558; 128/925, 898, 897

(56) References Cited

U.S. PATENT DOCUMENTS

| | | |
|---|---|---|
| 4,102,564 | 7/1978 | Michael . |
| 4,373,787 | 2/1983 | Crane et al. . |

(List continued on next page.)

OTHER PUBLICATIONS

Guitton, D., H.A. Buchtel, and R.M. Douglas. Frontal lobe lesions in man cause difficulties in suppressing reflexive glances and in generating goal–directed saccades. *Exp. Brain Res.* (1985) 58:455–472.

Munoz, DP (1997) Attentional and Psychiatric Influences on Gaze. Abstract, North American Neuro–ophthalmology Society. pp. 237–240.

Munoz, DP, Hampton, KA, Moore, KD, Goldring, JE (1999) Control of purposive saccadic eye movements and visual fixation in children with attention–deficit hyperactivity disorder. In: Current Oculomotor Research: Physiological and Psychological Aspects. Eds. W. Becker, H Deubel, T Mergner, Plenum. pp. 415–423.

Munoz, DP, Broughton, JR, Goldring, JE, Armstrong, IT (1998) Age–related performance of human subjects on Saccadic eye movement tasks. Exp. Brain Res. 121:391–400.

*Primary Examiner*—George Manuel
(74) *Attorney, Agent, or Firm*—Stephen J. Scribner; Carol Miernicki Steeg

(57) ABSTRACT

An apparatus for diagnosing or treating a neurological disorder, usually associated with a lack of attentiveness, in a subject by detecting the subject's eye movement. The apparatus includes a helmet for blocking visual stimuli from the subject's visual field; at least three visual cues disposed inside the helmet within the visual field of the subject when the helmet is placed on the subject's head, the visual cues capable of being switched from on to off states; at least two electrodes for attaching to the subject's face, the electrodes producing electrical signals corresponding to the subject's eye movements; signal processing means for controlling on and off states of the visual cues, receiving and processing electrical signals produced by the electrodes, and producing output signals corresponding to the subject's eye movements; and means for displaying output signals produced by the signal processing means. Methods are provided for diagnosing and treating a neurological disorder in a subject, using an apparatus according to the invention, comprising determining, in accordance with a selected test, whether the direction of the subject's eye movement in response to the switching on of either the left or the right visual cue is correct. After a prescribed number of trials, a score corresponding to the total number of correct eye movements is obtained, wherein the score is diagnostic of the neurological disorder. Treatment involves providing appropriate reinforcement in response to correct and/or incorrect eye movements.

32 Claims, 8 Drawing Sheets

U.S. PATENT DOCUMENTS

| | | |
|---|---|---|
| 4,889,422 | 12/1989 | Pavlidis . |
| 5,070,883 | 12/1991 | Kasahara . |
| 5,295,491 * | 3/1994 | Gevins .................................. 600/544 |
| 5,305,764 | 4/1994 | Yamada et al. . |
| 5,549,118 * | 8/1996 | John et al. ........................... 600/554 |

* cited by examiner

A   Anti-Saccade Task

B   Gap condition

METHOD AND APPARATUS FOR DETECTING EYE MOVEMENT

RELATED APPLICATIONS

This application claims the benefit of priority of U.S. Provisional Patent Application No. 60/119,641, filed Feb. 11, 1999, the content of which is incorporated herein by reference in its entirety.

FIELD OF THE INVENTION

This invention relates to a portable apparatus for measuring eye movement of subjects, and to methods for diagnosing and treating neurological disorders using such an apparatus.

BACKGROUND OF THE INVENTION

Information relating to eye movement and eye position is useful for the diagnosis of many neurological conditions, such as dyslexia. A number of devices for obtaining such data have been described, many of which include eye position sensors based on variations of the Purkinje eye tracker, wherein a light beam is applied to each eye and the light reflected from the eyes is used to determine eye position. In a device for measuring eye position described in U.S. Pat. No. 4,889,422, issued Dec. 26, 1989 to Pavlidis, a frame is provided for holding a subject's head, to prevent relative movement between the head and eye position sensors. U.S. Pat. No. 5,070,883, issued Dec. 10, 1991 to Kasahara, relates to an eye movement detecting apparatus to be worn on the head of an individual being tested, to overcome the problem of relative movement between eye position sensors and the head. U.S. Pat. No. 5,305,764, issued Apr. 26, 1994 to Yamada et al., describes a device for measuring eye and head movement of a subject, so that the line-of-sight of an individual may be detected. Further devices are described in U.S. Pat. Nos. 4,373,787, issued Feb. 15, 1983 to Crane, and No. 4,102,564, issued Jul. 25, 1978 to Michael.

The above-mentioned prior art devices are similar in that they provide precise information regarding the position or movement of the eyes themselves. As these devices rely on delicate and sensitive eye position detectors to provide the information, they are complex, and the delicacy of the detectors limits their portability.

Diagnosis of some neurological disorders may not require detailed information regarding eye position. Attention-deficit hyperactivity disorder (ADHD) is one such neurological condition, characterized by inattentiveness, impulsiveness, and hyperactivity. In the diagnosis of ADHD, data relating simply to eye movement would suffice and, in such cases, the above-mentioned prior art devices are not appropriate owing to their complexity of construction and usability.

Moreover, the diagnosis of ADHD, as with any neurological disorder, is ideally carried out with young children, so that corrective measures can begin at an early age. To do this, it would be most advantageous to have a device which could be both portable and inexpensive so that it could be taken to schools to screen children and operated by school personnel after minimal training. However, as mentioned above, existing instrumentation available to test eye movement is usually very expensive, not portable, and difficult to use.

OBJECT OF THE INVENTION

It is an object of this invention to provide a simple, inexpensive, and portable apparatus for diagnosing neurological disorders in individuals on the basis of eye movements.

It is a further object of this invention to provide methods for diagnosing and treating neurological disorders in individuals on the basis of eye movements.

SUMMARY OF THE INVENTION

In a first broad aspect, the invention provides an apparatus for diagnosing a neurological disorder in a subject by detecting the subject's eye movement. The apparatus includes: a helmet for blocking visual stimuli from the subject's visual field; at least one visual cue disposed inside the helmet within the visual field of the subject when the helmet is placed on the subject's head, the visual cue capable of being switched from on to off states; at least two electrodes for attaching to the subject's head, the electrodes producing electrical signals corresponding to the subject's eye movements; signal processing means for controlling on and off states of the visual cues, receiving and processing electrical signals produced by the electrodes, and producing output signals corresponding to the subject's eye movements; and means for displaying output signals produced by the signal processing means.

In a preferred embodiment, the at least one visual cue is at least three visual cues. The at least three visual cues are disposed inside the helmet within the visual field of the subject when the helmet is on the subject's head, and are located at the center, left, and right of the subject's visual field.

The signal processing means and display means may be disposed on the helmet. The signal processing means may comprise: at least one amplifier for amplifying the electrical signals produced by the electrodes; an A/D converter for receiving the output from the amplifier and producing a digital signal therefrom; and logic circuitry for processing the digital signal, controlling illumination of the visual cues, and producing output signals corresponding to the subject's eye movements. In certain embodiments of the invention, the A/D converter is disposed on/in the helmet, and the logic circuitry and display means are separate from the helmet. In the latter case, the logic circuitry and display means comprise a personal computer.

In some embodiments of the invention, at least one sound-emitting device is disposed within the helmet, wherein the sound-emitting device is controlled by the signal processing means. Preferably, two sound-emitting devices are disposed within the helmet, one adjacent each of the subject's ears when the helmet is on the subject's head.

In another broad aspect, the invention provides a method for diagnosing a neurological disorder in a subject. The method includes the following steps: (a) providing at least three visual cues within the subject's visual field while blocking any other visual stimuli from the subject's visual field, the visual cues capable of being switched from on to off states; (b) switching on the central visual cue; (c) switching off the central visual cue and switching on either one of the left or right visual cues; (d) switching off the left or right visual cue and switching on the central visual cue, wherein the subject is instructed to look at the central visual cue and then away from whichever of the left or right visual cues is subsequently switched on; (e) measuring the direction of eye movement in response to the switching on of either the left or right visual cue; (f) determining whether the subject's eye movements were as instructed; (g) repeating steps (b) to (f) a prescribed number of times; and (h) obtaining a score of the total number of correct or incorrect eye movements; wherein the score is diagnostic of the disorder and wherein an apparatus as described above for the first broad aspect of the invention is employed.

In a further broad aspect, the invention provides a method for treating a neurological disorder in a subject. The method includes the following steps: (a) providing visual cues within the left, right, and center of the subject's visual field while blocking any other visual stimuli from the subject's visual field, the visual cues capable of being switched from on to off states; (b) switching on the central visual cue; (c) switching off the central visual cue and switching on either one of the left or right visual cues; (d) switching off the left or right visual cue and switching on the central visual cue, wherein the subject is instructed to look at the central visual cue and then away from whichever of the left or right visual cues is subsequently switched on; (e) measuring the direction of eye movement in response to the switching on of either the left or right visual cue; (f) determining whether the subject's eye movements were as instructed; (g) providing positive reinforcement if the subject's eye movement was correct and/or negative reinforcement if the subject's eye movement was incorrect; and (h) repeating steps (b) to (f) a prescribed number of times. In some embodiments, the method also includes the step of obtaining a score of the total number of correct or incorrect eye movements, wherein reinforcement is provided depending on said score.

Neurological and psychiatric disorders associated with a lack of attentiveness which may be diagnosed, studied or treated with the apparatus or methods of the invention include, without limitation, attention deficit disorder (ADD) and attention-deficit hyperactivity disorder (ADHD), focal lesions, dyslexia, autism, schizophrenia, Parkinson's disease, Huntington's disease, Alzheimer's disease, progressive supranuclear palsy, cerebellar disorders, basal ganglia disorders, and organic disorders of the frontal lobes of the brain.

BRIEF DESCRIPTION OF THE DRAWINGS

Embodiments of the invention will now be described, by way of example, with reference to the accompanying drawings, wherein.

DETAILED DESCRIPTION OF THE INVENTION

Figure 1:
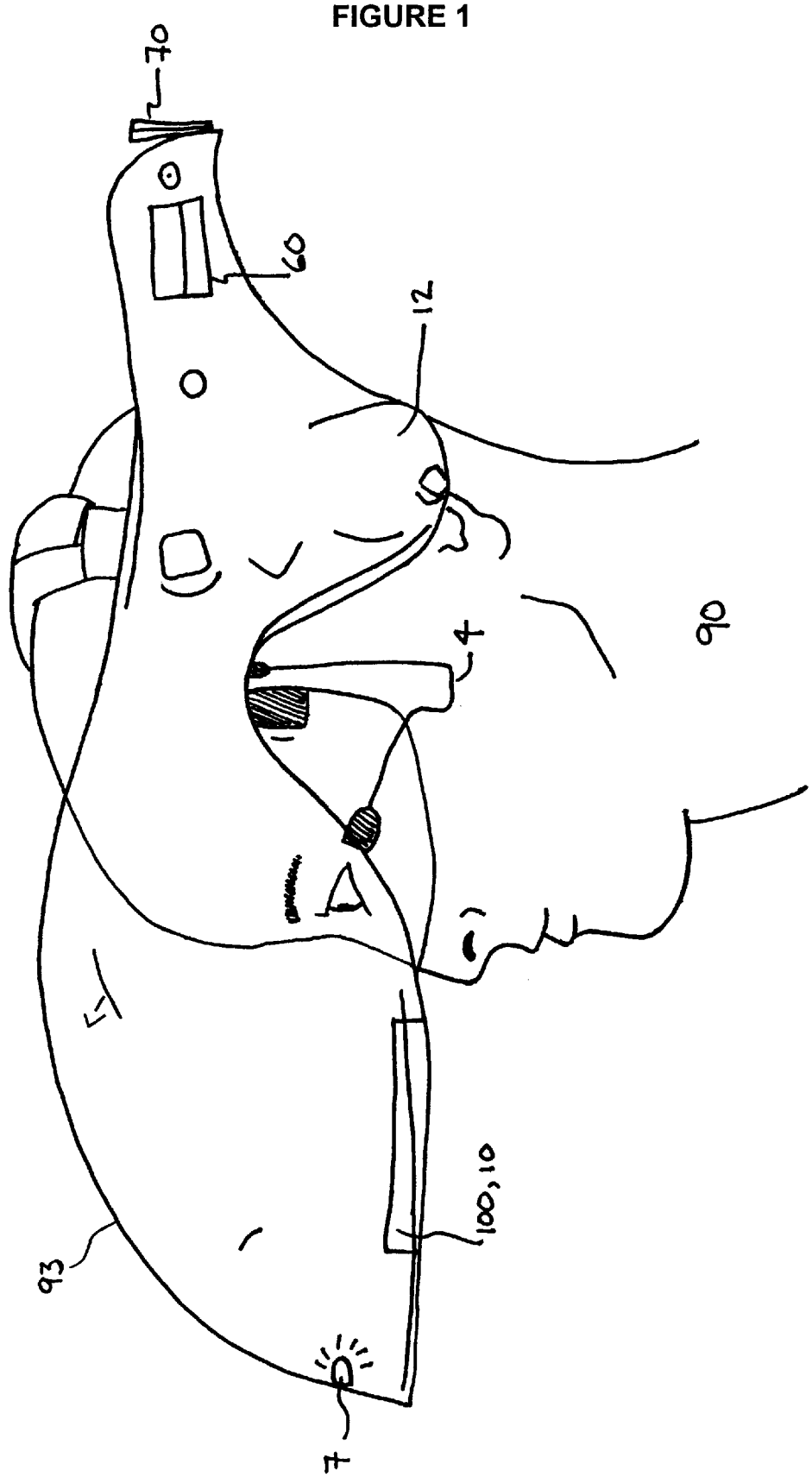
FIG. 1 is a side view of an apparatus according to the invention.

Saccades are rapid eye movements that are used to shift the visual axis from one target of interest to another. Between saccades, the visual axis is kept aligned on the target while the visual system performs a detailed analysis of the image. Several brain areas are involved in the control of visual fixation and saccadic eye movements, including regions within the cerebral cortex (posterior parietal and frontal cortex), basal ganglia (caudate, substantia nigra), thalamus, superior colliculus, brainstem reticular formation, and cerebellum. Because the areas span almost the entire neuraxis, there is considerable likelihood that neurological immaturity, degeneration, or malfunction alters the ability to control visual fixation and generate accurate saccades. Indeed, many clinical disorders and neurological diseases are characterized by abnormalities in the control of saccades and visual fixation in affected individuals. Examples of neurological and psychiatric disorders include disorders associated with a lack of attentiveness such as attention deficit disorder (ADD) and attention-deficit hyperactivity disorder (ADHD), focal lesions, dyslexia, autism, schizophrenia, Parkinson's disease, Huntington's disease, Alzheimer's disease, progressive supranuclear palsy, cerebellar disorders, basal ganglia disorders, and organic disorders of the frontal lobes of the brain.

In particular, ADD and ADHD are debilitating diseases characterized by symptoms including impulsiveness, inattentiveness, and in the case of ADHD, hyperactivity. These conditions affect approximately 5% of all North American school-aged children, where the symptoms often lead to behavioural difficulties in the classroom. The symptoms are chronic and affected children must develop strategies to help them cope with their life-long disability. Currently, however, the diagnosis of ADD and ADHD depends on several behavioural and psychological evaluations that are prone to subjective biases.

Current knowledge respecting abnormalities in control of eye movements in individuals affected with such neurological disorders is based entirely on data collected with laboratory instrumentation that has been optimized for accuracy and types of data that can be collected, and is therefore expensive, cumbersome to don, bulky to move, and too complex for use by non-technical personnel. In particular, such equipment is designed to produce precise quantitative measurements of eye movements in terms of eye position. The present invention is based, at least in part, on the realization that diagnosis of neurological disorders such as ADD and ADHD requires a measure of the direction of eye movements, rather than precise positioning.

In accordance with one aspect of the present invention, there is provided an apparatus for diagnosing a neurological disorder in a subject by detecting the subject's eye movement. An apparatus according to the invention enables rapid, reliable measurement of the direction of eye movement, and is portable and easy to use. An apparatus according to the invention comprises a helmet for blocking visual stimuli from the subject's visual field; visual cues disposed inside the helmet within the visual field of the subject when the helmet is placed on the subject's head, the visual cues capable of being switched from visible (on) to invisible (off) states; at least two electrodes for attaching to the subject's head, the electrodes producing electrical signals corresponding to the subject's eye movements; and processing circuitry. The electrodes are preferably attached to the subject's face so as to be able to monitor the movements of facial or eye muscles associated with eye movements. Preferably, the processing circuitry controls on and off states of the visual cues, receives and processes electrical signals produced by the electrodes, produces output signals corresponding to the subject's eye movements, and displays the output signals. An apparatus in accordance with the invention can have disposed therein any number of visual cues, the number being appropriate for a particular diagnostic test being used, as well as for a particular neurobiological disorder. Data relating to eye movements obtained with an apparatus of the invention can be used to diagnose neurological disorders including, but not limited to, those listed above.

The invention therefore provides an apparatus which is portable, inexpensive, and easy to use, such that, for example, it can be taken to schools to screen children, where it would be operated by school personnel after minimal training. Further applications include use by psychological councilors and pediatricians, and in neurology and psychiatric clinics, such that screening for disorders such as ADD and ADHD can be carried out in their offices. The invention is also applicable to clinical studies of new treatment regimes.

By another aspect, the present invention provides methods for diagnosing neurological disorders based on the detection of eye movement and employing the apparatus of the invention. According to the methods of the invention, the directions of eye movements of subjects performing various oculomotor tests are recorded and evaluated. Subject performance can be contrasted with that of age-matched controls (i.e., data obtained from individuals known to not have the disorder under investigation) to identify parameters which indicate the disability. In a preferred embodiment, the inventive method provides a simple, two-choice anti-saccade test, enabling its widespread use as a diagnostic and evaluative aid. In the case of ADHD, data obtained from children show that eye movement monitoring using conventional equipment provides a useful tool to assist in the diagnosis of the disorder (Munoz 1997).

By yet another aspect of the invention, there is provided a method for treating neurological disorders associated with abnormalities in the control of eye movements. As used herein, the term "treating" is intended to mean reducing, mitigating, and/or ameliorating symptoms of the disorder in an individual. The method involves monitoring an individual's performance on one or more eye-movement tasks, and providing positive reinforcement for correct saccades, and/or negative reinforcement for incorrect saccades. An example of a suitable eye-movement task that may be employed is the two-choice anti-saccade test, mentioned above and described in detail below. The method of treatment of the invention is based on the premise that such reinforcement leads to an improvement (i.e., reduction, mitigation, and/or amelioration of the symptoms of a disorder) in an affected subject. In a preferred embodiment, the invention provides a method of treating ADD and ADHD, using the anti-saccade test. In carrying out the method of treating a neurological disorder associated with abnormalities in the control of eye movements, such as, e.g., ADD or ADHD, an apparatus in accordance with the present invention can advantageously be employed.

The method and apparatus of the present invention are also applicable to developing, monitoring, and evaluating drug therapy for conditions such as ADD and ADHD. For example, treatment of ADHD with drugs such as methylphenidate (Ritalin™) appears to be effective in at least some cases, but is controversial. Because of the current subjective nature of the diagnosis, it is likely that many children receive the drug inappropriately. Furthermore, heretofore there has been no objective measure to adjust or optimize dosage to maximize therapeutic effect while minimizing side-effects. The invention provides a simple means to monitor the response of a subject during a trial course of drug therapy. This is useful both for partial confirmation of the diagnosis according to the response to the drug and for appropriately adjusting the dosage of the drug.

It is emphasized that, while the present invention is described primarily with respect to ADD and ADHD, the invention is not limited to diagnosis of these disorders, and it may be applied to any disorder or condition which lends itself to diagnosis by way of eye movement testing. These can be any other clinical disorders or neurological diseases that produce abnormalities in control of eye movements, including, but not limited to, attention deficit disorder (ADD), attention-deficit hyperactivity disorder (ADHD), focal lesions, dyslexia, autism, schizophrenia, Parkinson's disease, Huntington's disease, Alzheimer's disease, progressive supranuclear palsy, cerebellar disorders, basal ganglia disorders, and organic disorders of the frontal lobes of the brain. Thus, while a test for diagnosing ADD and ADID is described below, it will be apparent to those skilled in the art that the test, or in some cases variations thereof, can also be used to diagnose the above-mentioned neurological disorders. Such variants fall within the scope of the present invention.

Figure 2:
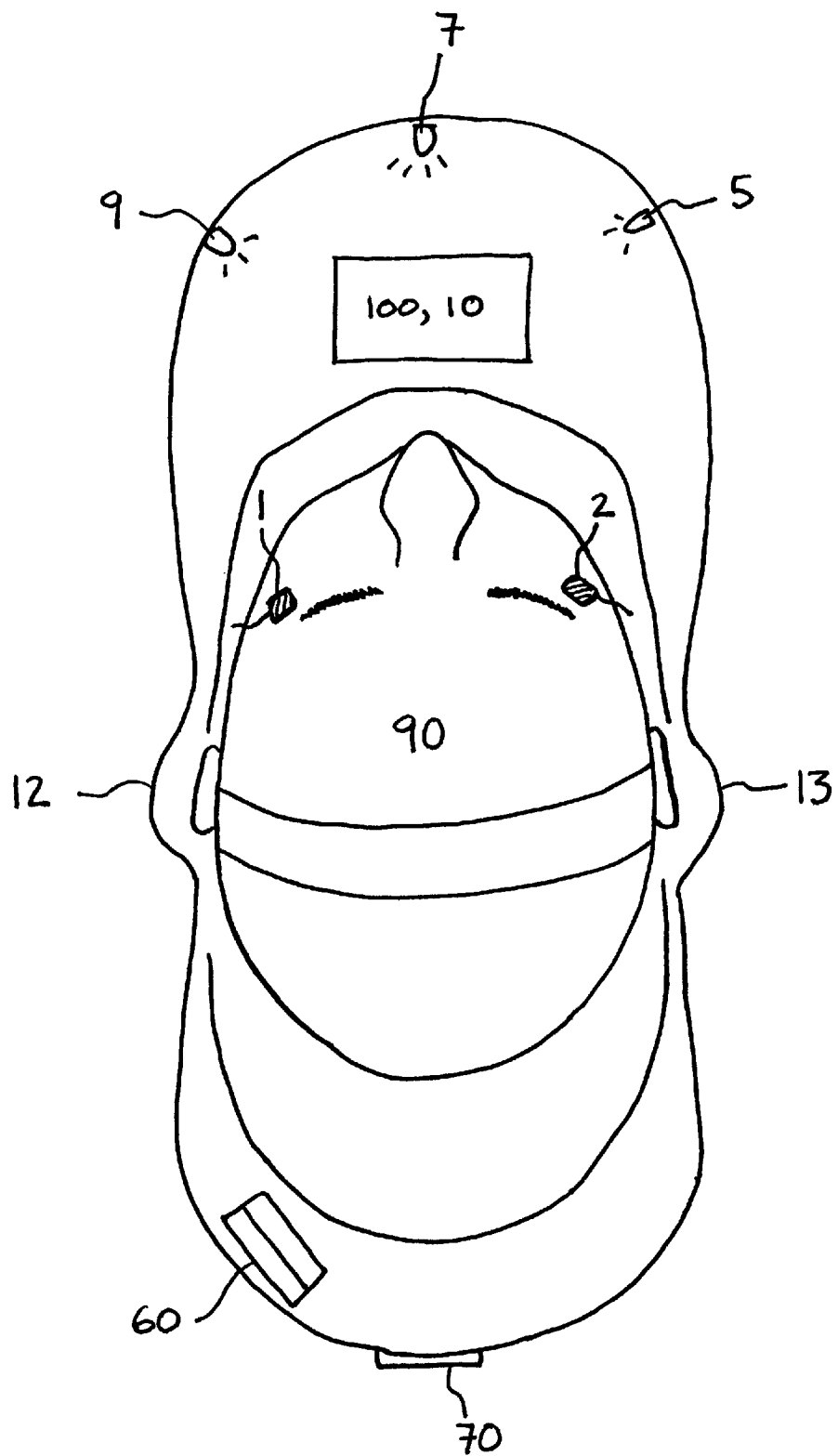
FIG. 2 is a plan view of an apparatus according to the invention.

As shown in FIGS. 1 and 2, an apparatus according to a preferred embodiment of the invention consists principally of a helmet 93 worn by subject 90 during testing. Preferably, the helmet 93 is provided with adjustable straps or the like so that it can be fitted comfortably and snugly to any subject's head. As used herein, "helmet" is intended to mean any form of headgear that, when worn on the subject's head, substantially encloses the subject's visual field, and which can accommodate, at least, the visual cues described below. A helmet in accordance with the invention may be of any shape and size, and may enclose any portion of the subject's head. Thus, a helmet according to the invention can be as simple as, for example, a pair of goggles, or as elaborate as a full helmet. According to a preferred embodiment, the helmet blocks substantially all ambient light from entering the subject's field of view, so that the subject sees visual cues (described below) against a dark background. Alternatively, if desired, the helmet may provide to the subject a field of view of any appropriate intensity of light. What is important is that the helmet allows the subject to see the visual cues and simultaneously prevents the subject from seeing any distracting visual stimuli.

Visual cues are provided inside the helmet 93 within the subject's field of view. The visual cues are presented to the subject to elicit eye movements, and may be of any form, provided they can be switched from an "off" state to an "on" state. Preferably "off" is substantially invisible and "on" is substantially visible, but other binary states, e.g., blue/yellow, slow blinking/rapid blinking, are also encompassed in the scope of the invention. In the off state of the preferred embodiment, a visual cue will be invisible if, for example, it simply can't be seen because of the darkness presented to the subject's visual field when wearing the helmet, or it blends in with its background. The number and arrangement of visual cues can vary according to factors such as the type of disorder being diagnosed, the test being used (e.g., countermanding task, anti-saccade task, etc., see below). Thus, visual cues can be provided in any combination of the center, left, right, top, bottom, or anywhere between these, of a subject's field of view.

Light sources such as light-emitting diodes (LEDs) are particularly well suited to for use as visual cues. The visual cues may all be the same colour, or arranged in any combination of colours, as desired for particular tests (discussed below). In some circumstances, such as in the case of any of the various types of colour-blindness that may affect an individual being tested, it is desirable to have visual cues of a particular colour. Multi-coloured LEDs, such as bicoloured LEDs, can advantageously be used, and the helmet configured to easily change the colour of one or more of the visual cues as required.

In a preferred embodiment of the present invention, shown in FIG. 2, visual cues, for example LEDs, are located at the center, left, and right of the subject's visual field, shown as the center LED 7, left LED 9, and right LED 5. That is, the center LED is positioned such that, when a subject is looking at it, the subject will be looking substantially straight ahead. The left and right LEDs are positioned such that when looking at either LED, the subject's eyes will shift (i.e., saccade) to the left or right, as the case may be, about 10° to 25°, preferably about 12° to 17°, from the straight ahead position.

As shown in FIGS. 1 and 2, one or more sound-emitting devices 12,13, such as loudspeakers, piezo-electric devices, or the like, may optionally be provided in the helmet 93, to provide audio signals to the subject 90. Electrodes attached to the subject's head provide electrooculogram (EOG) signals generated by eye movements. In a preferred embodiment shown in FIGS. 1 and 2, two skin surface electrodes are affixed to the face, electrode 1 at the lateral margin of the left eye and electrode 2 at the lateral margin of the right eye, so as to provide EOG signals corresponding to light and right eye movements. However, in other embodiments where, for example, visual cues are provided at the top and bottom of a subject's visual field, the electrodes would be attached above and below the subject's eyes. Disposable, self-adhesive electrodes, such as those available from The Electrode Store© (P.O. Box 188, Enumclaw, Wash. 98022) are suitable. Alternatively, the subject 90 may be fitted with a headband (not shown) to hold electrodes in position against the skin of the face. Those skilled in the art will recognize that any suitable style of electrode may be employed, so long as EOG signals are generated in the electrodes as a result of eye movements.

Figure 3:
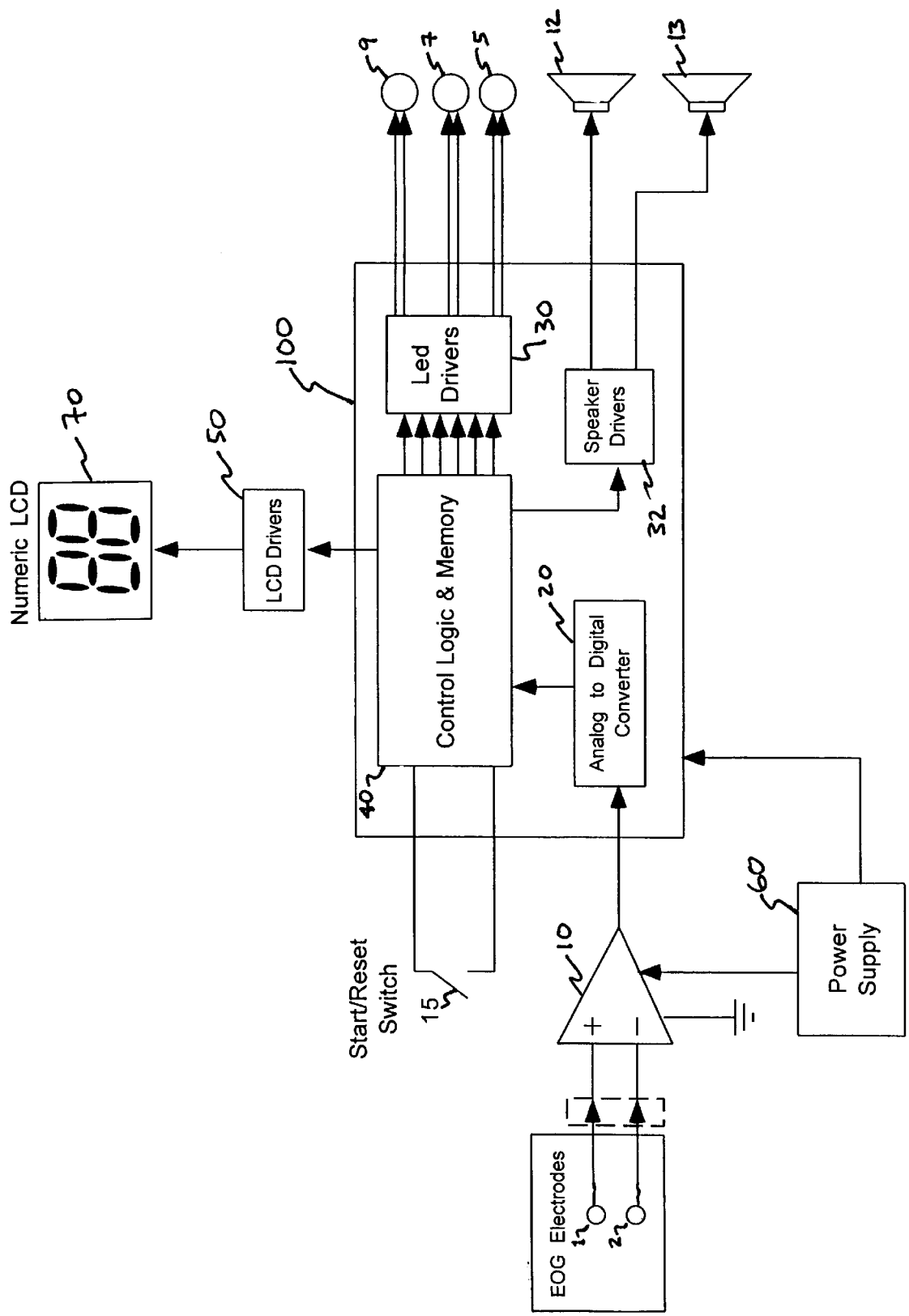
FIG. 3 is a block diagram showing an embodiment of circuitry of the invention.

According to a preferred embodiment shown in FIGS. 1 to 3, all of the processing circuitry is mounted on, or in, the helmet 93. EOG signals generated in the electrodes are input to a preamplifier 10 via suitable wires 4 and connectors as are well known in the art. Preamplifier 10 is preferably mounted on the helmet 93, to minimize the length of the connecting wires from the electrodes 1,2. The preamplifier 10 amplifies electrical signals produced by the electrodes, and provides an output signal which is input to circuitry 100. The circuitry 100 provides an output which is displayed on a display device 70, which display device may be a liquid crystal display (LCD) or LED display, or any other suitable display. For example, a two-digit LCD display, each digit having seven segments, is suitable. Of course, if more or less information is to be displayed, a display having any number of digits and segments can be employed.

It should be noted that any of the processing circuitry can be separate from the helmet and hence can communicate with the helmet via suitable cables and connectors, or via radio waves. However, it is preferred that the preamplifier be mounted on the helmet, as the EOG signals from the electrodes are typically of a low level and the length of cables connecting the electrodes to the amplifier should be kept as short as possible to minimize interference. Power for all of the electronic components is provided by a power supply 60 also disposed on the helmet. The power supply 60 can be a primary or rechargeable battery, or an external power supply such as an AC to DC converter.

Arrangement of electronic components according to a preferred embodiment of the invention is shown diagrammatically in FIG. 3, and in detail in the Working Example below. As can be seen from FIG. 3, circuitry 100 includes control logic 40 for controlling on and off states, via LED drivers 30, the center 7, left 9, and right 5 LEDs. A reset switch 15 is provided for fundamental control of the control logic circuitry. Eye movements produce EOG signals which are amplified by the preamplifier 10 (e.g., a differential amplifier). As the EOG signals are typically very low-level signals, the preamplifier 10 is advantageously located physically separate from circuitry 100 to reduce electrical interference therefrom. The amplified EOG signals enter circuitry 100 where they are digitized by an analogue-to-digital converter 20. Directions of eye movement (e.g., center, left, right) at particular times after the presentation of each visual cue are determined by a movement detection algorithm in control logic and memory circuitry 40. The control logic also controls the optional sound emitting devices 12,13 via drivers 32. The control logic is connected, via drivers 50, to display device 70, which may be any suitable device such as a liquid crystal display. As discussed in detail in the Working Example, the display 70 can provide information such as whether a particular eye movement was a valid (i.e., quantifiable) response to a given cue, the direction of eye movements, and scores such as the number of correct, incorrect, invalid, and/or erroneous responses to a number of visual cues.

The processing circuitry can be implemented with various combinations of discrete components, or at various levels of electronic integration, through the use of available and custom integrated circuits. It is preferred that a single microprocessor is employed, the microprocessor capable of being programmed to perform algorithms for any test of interest. For example, the presentation of visual cues, detection of eye movement, optional presentation of audio cues, accumulation of score, and generation of displays on the display device 70 are all functions that can be carried out by a microprocessor. Depending on the capabilities of the particular microprocessor selected, all or most of the functions enumerated separately within electronic circuitry 100 can be performed by the microprocessor, with additional discrete components as required. Those skilled in the art will recognize that there are a multitude of different configurations of electronic components such as discrete components, programmable gate arrays, microcontrollers, application-specific integrated circuits, and personal computer chips that could be substituted to provide substantially equivalent functions of the preamplifier 10 and circuitry 100, within the scope of this invention. In cases where at least a portion of the processing circuitry is not disposed on the helmet, a discrete computer (e.g., a personal computer, such as a laptop computer for portability), can be employed for performing any of the required functions, and for storing and executing additional algorithms.

It is preferred that a calibration procedure is run before beginning an actual test trial, to deal with variations in the amplitude of the EOG signal from subject to subject. The calibration procedure involves recording and storing the subject's saccades between the visual cues, as discussed in detail in the Working Example below. Preferably, the calibration procedure is implemented with a microprocessor. A microprocessor-based implementation enables the same hardware to perform variations of the eye-movement task beyond the anti-saccade task described in detail below and in the Working Example. For example, the microprocessor can contain several different tests in its nonvolatile memory and the operator can select which test to present via the reset button. The display 70 can display a code indicating which program is currently selected. Further options for different programs include, for example, changes in audio or visual feedback regarding correct performance of a task and changes in the number, colour, and timing of LEDs illuminated and/or in the instructions given verbally regarding the task (e.g., use of "gap condition", "overlap condition", or "distractor cues" as known in the art and/or discussed below).

The invention also contemplates a "slave" mode wherein the apparatus of the invention functions as a real-time input-output and data acquisition interface for a personal computer. In such a mode, for example, the computer can transmit information to the microcontroller in the helmet, specifying the timing of visual and/or audio stimulus presentations and the data acquisition for a single trial; it then receives a buffer of data on eye movements during that trial. The computer then performs the scoring and can incorporate more complex sequences of trials that may be conditional on results to date or input from an observer.

Figure 4:
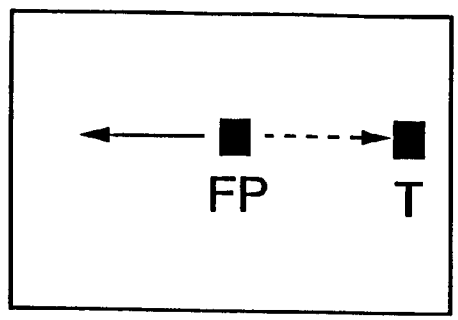
FIG. 4 is a diagrammatic representation of the anti-saccade task.
Figure 4:
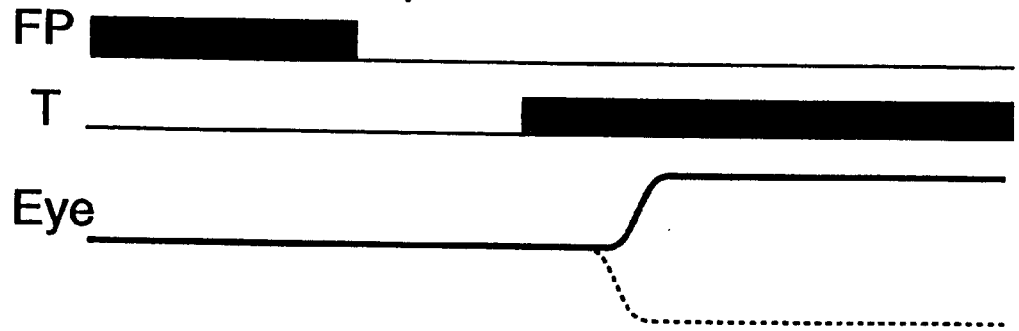

In a preferred embodiment, the invention is based on the anti-saccade task. The anti-saccade task (FIG. 4) is one task that probes the ability of a subject to generate a voluntary saccade after first suppressing a reflexive saccade (Hallett 1978). The subject initiates a trial by looking at a central fixation point (FP). Then, an eccentric target (T) appears randomly to the left or right. The subject is instructed to look from the central FP to the opposite side of the T (solid line). An error in performance is defined as a reflexive glance toward the eccentric target (dashed line). A gap period is imposed between the disappearance of the FP and the appearance of the T. This gap period forces subjects into a more reflexive mode of behaviour which challenges them to suppress reflexive responses. Thus, subjects are required to look away from an eccentric visual target that suddenly appears, rather than look towards it. To perform the anti-saccade task correctly, subjects must first suppress a reflexive glance to the eccentric target and then generate a voluntary movement to a location where no stimulus appeared. This task is very useful at assessing the ability of a subject to suppress an unwanted eye movement in the presence of a distracting stimulus. We have now used this task to study performance in both humans (Munoz et al. 1998, 1999) and non-human primates (Everling et al. 1998; 1999; Everling and Munoz 2000).

Guitton and colleagues (1985) were the first group to apply the anti-saccade task to a pathological condition. These authors found that patients with lesions of the lateral prefrontal cortex had difficulty performing the task correctly. Rather than look away from the eccentric stimulus (i.e., solid traces in FIG. 4) these patients could not suppress a reflexive glance to the eccentric stimulus (i.e., dashed traces in FIG. 4). Clinical studies have since verified that patients with pathophysiology affecting the frontal cortex and/or basal ganglia yield similar difficulties in performing the anti-saccade task (see Everling and Fischer 1998 for review).

Figure 5:
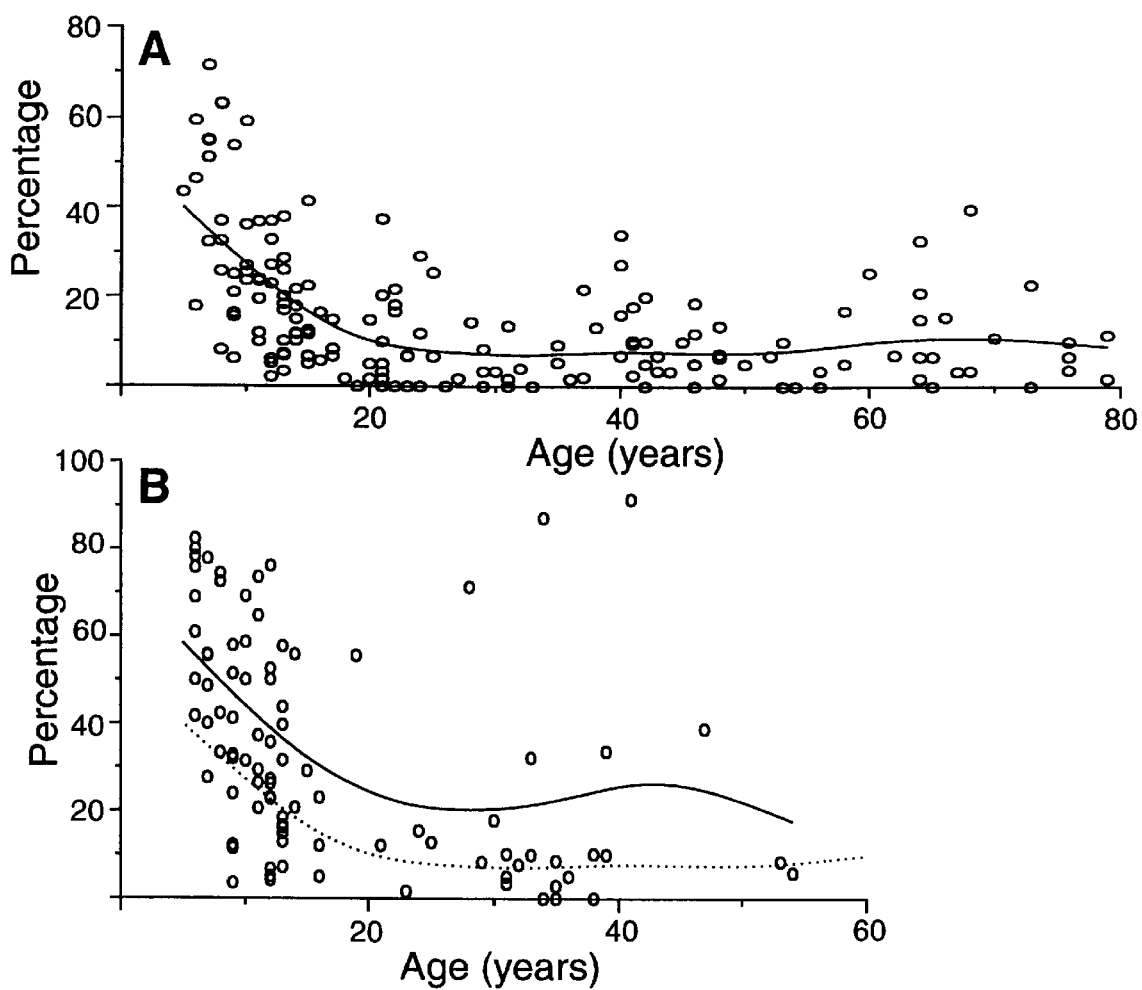
FIG. 5 shows the percentage of direction errors versus subject age for control (A) and ADHD (B) subjects performing the anti-saccade task.

FIG. 5 shows data obtained during recent work on human subjects in an eye-movement laboratory. The data of FIG. 5 were not obtained using the apparatus of the present invention, but are shown to illustrate how anti-saccade task data can be used to diagnose ADHD. FIG. 5 shows the percentage of direction errors versus subject age for control (A) and ADHD (B) subjects. The solid lines are curve fits through the data. The dashed line in B represents performance of age-matched control subjects. As a group, the ADHD subjects are significantly impaired relative to control subjects. However, note that some ADHD subjects are no different than age-matched control subjects. The data indicate that subject age plays a profound role in the ability to perform the anti-saccade task correctly (Munoz et al. 1998). Young children (<9 years of age) have considerable difficulty suppressing a reflexive glance to the peripheral stimulus (FIG. 5A). Task performance improves dramatically between the ages of 9 to 16 years and performance is stable between the ages of 16 to 80 years. The dramatic improvement in performance of the anti-saccade task that takes place between the ages of 6 to 16 years parallels the late maturation of the frontal cortex.

We have begun to apply the anti-saccade task to the study of children and adults diagnosed with attention-deficit hyperactivity disorder (ADHD) (Munoz et al. 1999). To date, we have studied 97 ADHD subjects (68 children, 29 adults) and 190 control subjects (71 children, 119 adults) in the anti-saccade task (see FIG. 5). In the anti-saccade task, ADHD subjects made significantly more direction errors than age-matched control subjects (FIG. 5B).

Figure 6:
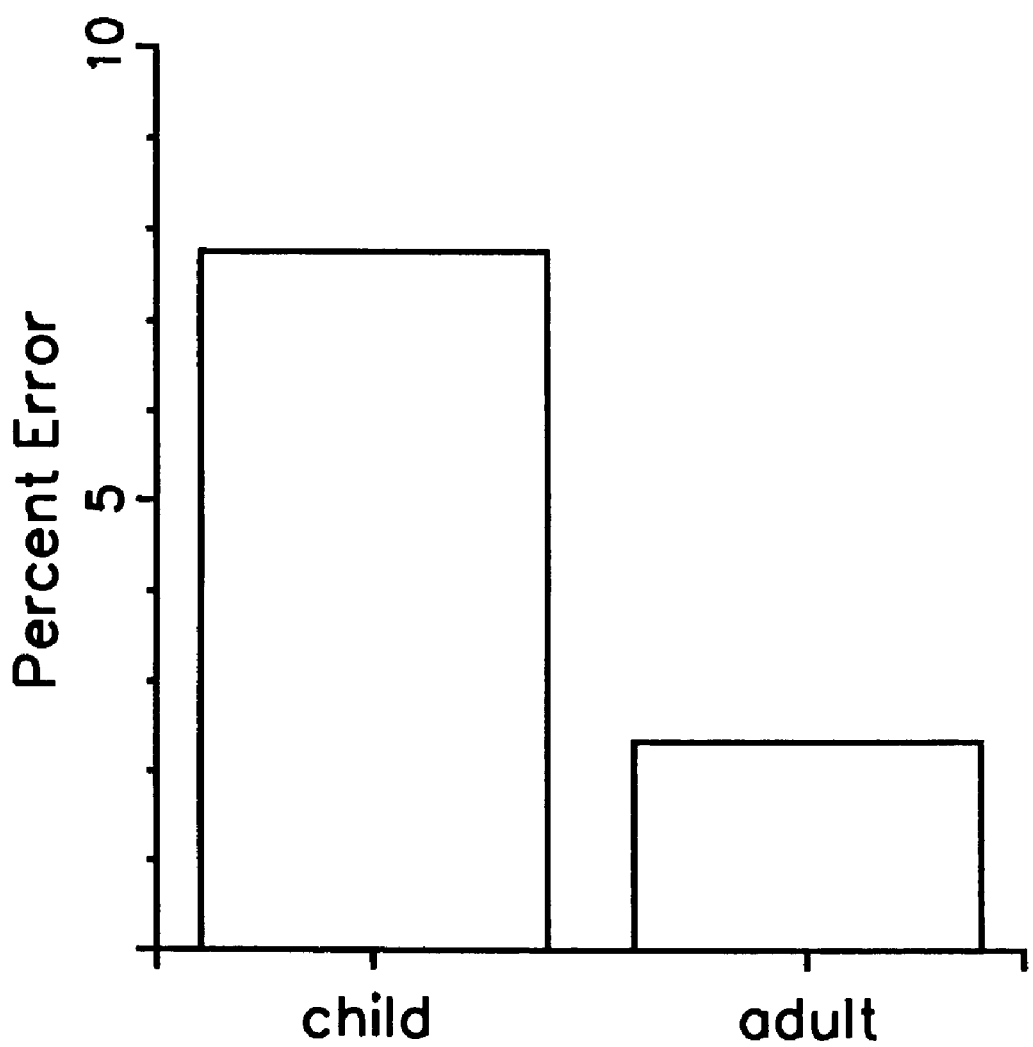
FIG. 6 shows anti-saccade performance data for 4 children and 2 adults using an apparatus according to a preferred embodiment of the invention.

FIG. 6 shows data collected from 6 subjects (4 children, 2 adults) known to not have ADHD, whose anti-saccade performance was determined using an apparatus according to a preferred embodiment of the invention (see the Working Example). The data show that children make more errors than adults, and in both groups the error rates are comparable to those obtained for normal individuals using elaborate eye movement laboratory equipment.

Figure 7:
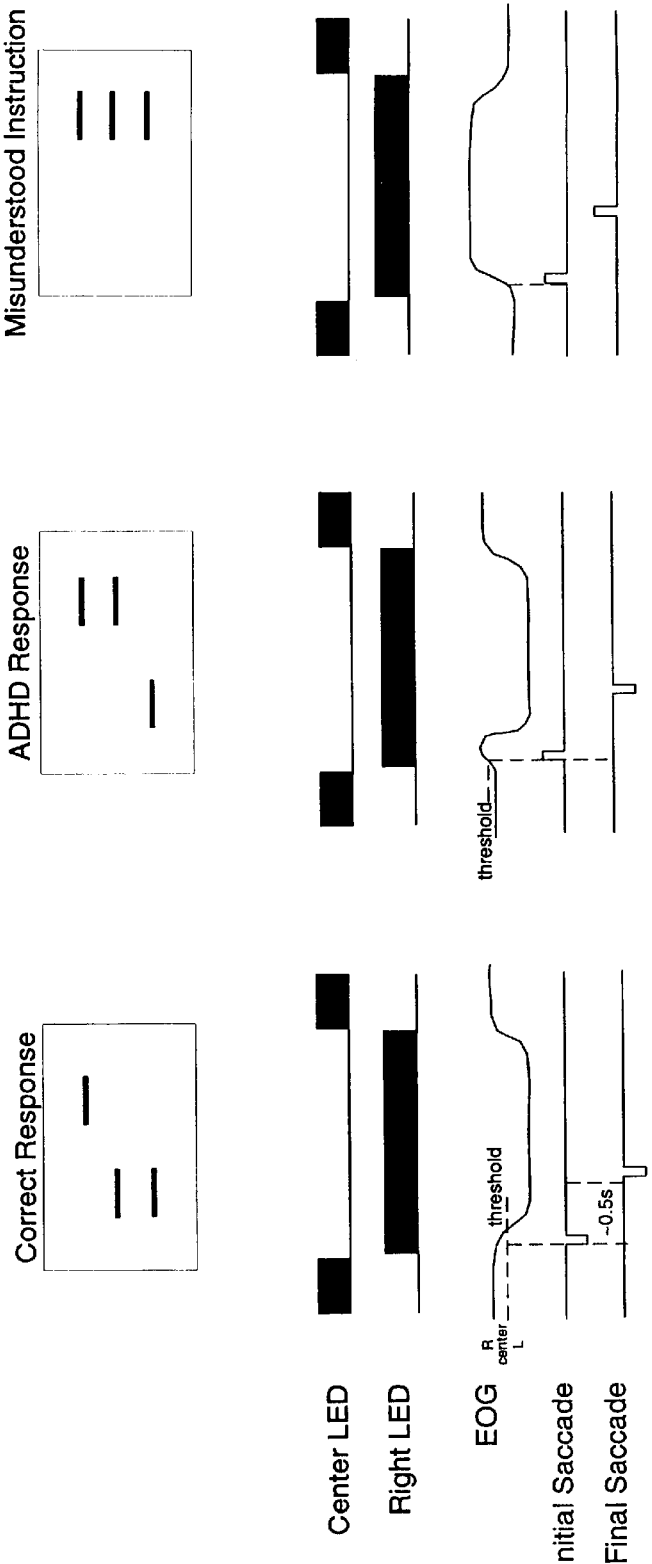
FIG. 7 shows examples of a display and corresponding timing diagram of a preferred embodiment of an apparatus of the invention.
Figure 8:
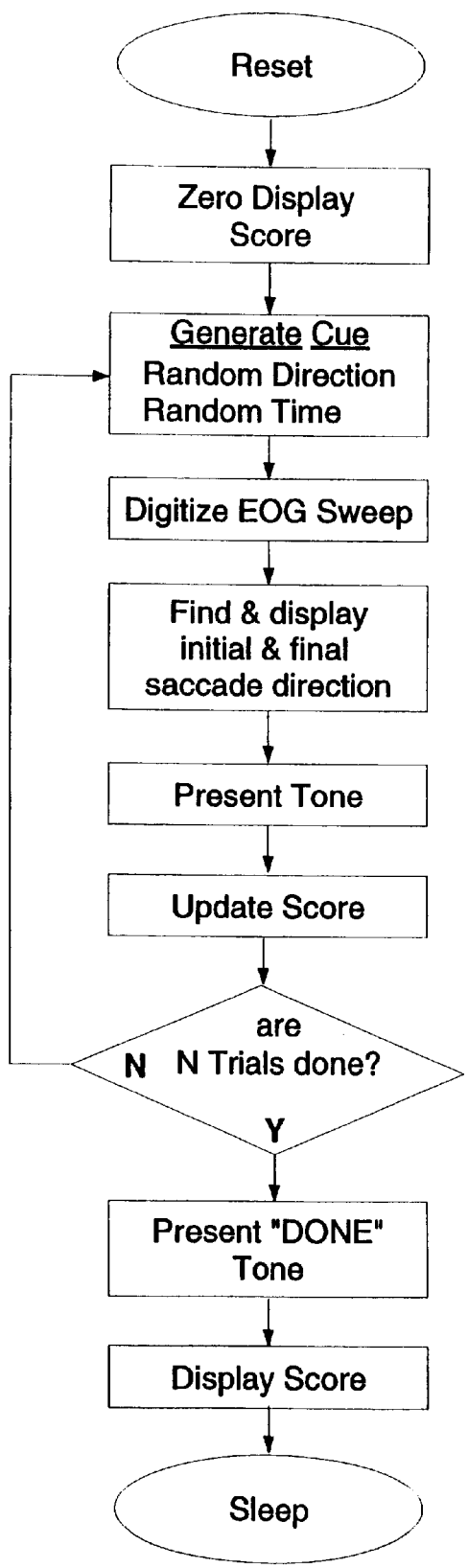
FIG. 8 is a flow chart depicting an algorithm in accordance with an apparatus of a preferred embodiment of the invention.

In accordance with an apparatus according to a preferred embodiment of the present invention, an example of a sequence of states and displays during a test, in this example an anti-saccade task, is shown pictorially in FIG. 7 and as a flow-chart in FIG. 8. Control logic and memory unit 40 is initialized by touching the reset switch 15, which clears the display 70. The center LED 7 is illuminated via LED driver 30. After a delay (e.g., 0.2 to 1.0 s), the length of which can be randomized, the central LED 7 is extinguished and one or the other of the left 5 or right 9 LEDs is illuminated at random. The subject 90 makes a saccadic eye movement according to the instruction to look away from the illuminated lateral LED. The EOG signal from preamplifier 10 is digitized by converter 20 for a period of approximately 1 s after the cue. Movement detection algorithm 22 identifies the initial direction of the saccade plus a final direction of the eyes approximately 0.5 s later, which may be the same or different. The movement detection algorithm 22 is advantageously performed digitally because it is likely to require various self-calibrating features to deal with inter-subject differences in EOG amplitude, electrical artefacts, and response timing. The direction of the cue, the initial saccade and the final eye direction are displayed to the operator on the display 70 as depicted in FIG. 7. If desired, the correct or incorrect nature of the initial saccade and/or the final eye position can be signalled to the subject by using tone generator 32 and sound-emitting device 12. At the end of each trial, the cue LED is extinguished and the central LED 7 is reilluminated so the subject can return to the starting position of looking straight ahead. After a preset number of trials, the total number of errors, defined as initially incorrect saccade directions, is displayed for the operator on display 70 and the electronic circuitry 100 enters a sleep or automatic power-off mode to conserve power. This embodiment is described in further detail in the Working Example.

The present invention also provides methods of diagnosing a neurological disorder in a subject using an apparatus in accordance with the invention. According to a preferred embodiment of the method, which is designed to diagnose ADD and ADHD and is described in detail in the Working Example, a subject performs an anti-saccade task. As discussed above, the subject is instructed to look at the central LED when it is on, then to immediately look (i.e., make a saccade) in a direction opposite to either of the lateral LEDs when it is illuminated, and then back to the central LED when it is turned back on. Both the delay before a lateral LED is illuminated and whether the left or right LED is illuminated are randomized to overcome guessing by the subject. Normal individuals can perform this task with high success rates (>80%). Subjects with uncontrolled ADHD generally make an initial incorrect saccade toward the illuminated LED and then rapidly reverse direction to correctly look away from the LED. When using embodiments of the apparatus in which loudspeakers or other sound-emitting devices are included, sound can be employed to provide positive or negative feedback to the subject, to instruct the subject in the correct performance of the task, or as an alternate source of directional cue. A typical anti-saccade task runs a fixed number of trials, such as, for example, 50 to 100 trials, and the display device of the apparatus displays the number of errors in initial saccade direction that occurred. As an aid to the operator, the device can be configured to display additional information, such as information about the target directions and the initial saccade and final eye directions detected by the apparatus on each trial.

By yet another aspect of the invention, there is provided a method for treating neurological disorders associated with abnormalities in the control of eye movements, such as attention deficit disorder (ADD), attention-deficit hyperactivity disorder (ADHD), focal lesions, dyslexia, autism, schizophrenia, Parkinson's disease, Huntington's disease, Alzheimer's disease, progressive supranuclear palsy, cerebellar disorders, basal ganglia disorders, and organic disorders of the frontal lobes of the brain. As used herein, the term "treating" is intended to mean reducing, mitigating, and/or ameliorating the symptoms of the disorder in an individual.

The method involves monitoring an individual's performance on one or more eye-movement tasks, and providing positive reinforcement for correct saccades, and/or negative reinforcement for incorrect saccades. A typical task runs a fixed number of trials, such as, for example, 50 to 100 trials. Suitable eye-movement tasks that may be employed include the saccadic reaction time (SRT) task and the anti-saccade task, as described herein. Positive reinforcement can be presented in the form of encouraging comments, music, sounds, rewards and the like, while negative reinforcement can be presented as negative versions of these. Of course, various forms of positive and negative reinforcement can be devised based on the age and interests of the individual under test, as is known in the art. The reinforcement can be provided after each trial, or at the end of the task. The method of treatment of the invention is based on the premise that such reinforcement leads to an improvement (i.e., reduction, mitigation, and/or amelioration of the symptoms of a disorder) in an affected subject. In a preferred embodiment, the invention provides a method of treating ADD or ADHD, using the anti-saccade test previously described. In carrying out the method of treating a neurological disorder associated with abnormalities in the control of eye movements, such as ADD or ADHD, an apparatus in accordance with the present invention can advantageously be employed.

As mentioned above, while the invention is described in connection with a preferred embodiment for diagnosing and treating ADD and ADHD, there are many other psychological and neurological disorders which can be diagnosed and treated through eye movement control. Many variations of such tests are possible with minor variations of the apparatus of the invention and reprogramming of the processing hardware described above. For example, the helmet can contain only a single visual cue, and a test involving detecting a break in a subject's visual fixation employed. In another example, the helmet could contain five visual cues (e.g., center; 10° left; 20 ° left; 10° right, 20°right) to allow for more unpredictablity with respect to the appearance of visual cues. Programming of alternative oculomotor tests can be accomplished by, for example, having a personal computer such as a laptop computer transmit new stimulus programs to battery-backed RAM in the microcontroller. The countermanding task (Hanes et al. 1995) is an example of such an alternative test, wherein subjects are instructed to look from the center to the eccentric visual cue, unless the center cue reappears, in which case the subject is required to inhibit the planned movement. The time between eccentric cue appearance and central cue reappearance is varied randomly between, for example, 0 to 300 ms to make it either easier or more difficult to inhibit the planned movement. In this model, subjects with frontal/basal ganglia disorders and related disorders are expected to have more difficulty inhibiting saccades on stop trials.

Another test to which the invention is applicable involves extracting the timing of a saccade relative to the appearance of a visual cue (saccadic reaction time (SRT)). According to this test subjects are instructed to look at the visual cues (pro-saccade mode), and the SRTs computed. The subjects are then instructed to look away from the visual cues (anti-saccade mode). Data corresponding to SRTs as well as anti-saccade direction errors can then be computed. There are also known differences in the SRT and direction errors depending upon the state of fixation at visual cue appearance. To manipulate fixation state the center cue can either remain on at eccentric cue appearance (overlap condition) or the center cue can disappear briefly (e.g., 200 ms) before cue appearance (gap condition).

WORKING EXAMPLE

The following example, in the form of an operator's manual, describes an embodiment of the invention suitable for carrying out the anti-saccade test, and a method for using this embodiment to diagnose ADHD.

EQUIVALENTS

Those skilled in the art will recognize, or be able to ascertain using no more than routine experimentation, many equivalents to the specific embodiments of the invention described herein. Such equivalents are intended to be encompassed by the following claims.

REFERENCES

Everling, S, Dorris, M C, Munoz, D P (1998) Reflex suppression in the anti-saccade task is dependent on pre-stimulus neural processes. J. Neurophysiol. 80:1584–1589.

Everling, S, Dorris, M C, Klein, R M, Munoz, D P (1999) Role of primate superior colliculus in preparation and execution of anti- and pro-saccades. J. Neurosci. 19:2740–2754.

Everling S, Fischer B (1998) The antisaccade: a review of basic research and clinical studies. Neuropsychologia 36:885–899.

Everling, S, Munoz, D P (2000) Neuronal correlates for preparatory set associated with pro-saccades and anti-saccades in the primate frontal eye field. J. Neurosci. 20:387–400.

Guitton D, Buchtel H, Douglas R (1985) Frontal lobe lesions in man cause difficulties in suppressing reflexive saccades and in generating goal-directed saccades. Exp. Brain Res. 58:455–472.

Hallett P (1978) Primary and secondary saccades to goals defined by instructions. Vision Res. 18:1279–1296.

Hanes et al. (1995) Countermanding Saccades in Macaque. Visual Neuroscience 12:929–937.

Munoz, D P (1997) Attentional and Psychiatric Influences on Gaze. Abstract, North American Neuro-ophthalmology Society. pp. 237–240

Munoz, D P, Broughton, J R, Goldring, J E, Armstrong, I T (1998) Age-related performance of human subjects on saccadic eye movement tasks. Exp. Brain Res. 121:391–400.

Munoz D P, Hampton K A, Moore K D, Goldring J E (1999) Control of purposive saccadic eye movements and visual fixation in children with attention-deficit hyperactivity disorder. In: Current Oculomotor Research: Physiological and Psychological Aspects. Eds. W Becker, H Deubel, T Mergner, Plenum. pp. 415–423.

HyperSpace Helmet™
Manual
January 19, 2000
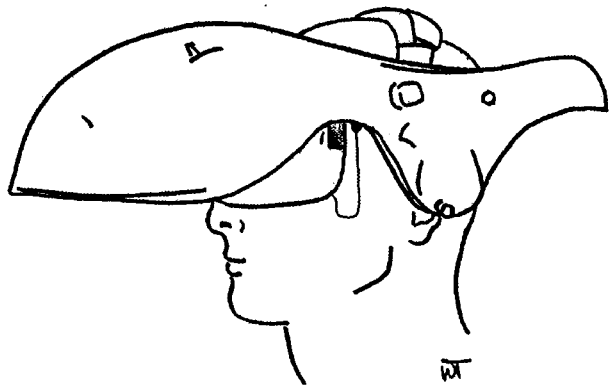
Preliminary Draft: CONFIDENTIAL
AUTHORS:
Chris Wellstood
Dr. G.E. Loeb
Barbara Lawson
Origin: MRC Group in Sensory-Motor Neuroscience
Tel: (613)533-2790
Email: chris@biomed.queensu.ca

Operator's Manual

*Overview*

The HyperSpace Helmet™ permits rapid screening and quantitative evaluation of eye movements for disorders that affect saccadic eye movements, such as attention-deficit/hyperactivity disorder (ADHD). Visual and/or auditory cues signal the subject to make horizontal eye movements that are monitored by electro-oculogram (EOG). A battery-operated microprocessor in the helmet records a score and displays the numeric results for the operator.

The HyperSpace Helmet™ can be operated in two modes:

1. Stand-Alone Mode:

In stand-alone mode, the microprocessor runs a preset paradigm called the anti-saccade task. Before beginning the paradigm, the EOG must be calibrated. To calibrate, the subject must look directly at the lights as they appear. Once calibration is completed, the subject is told to look at the centre light whenever it is on but to look *away* from the lateral target lights, which come on to the right or left randomly. Most subjects do so correctly most of the time, but subjects with ADHD tend first to make a brief movement toward the target before reversing to look correctly away from it. The display on the outside of the helmet shows the direction of the target light and the saccades for each trial so that the operator can see if the subject seems to understand the task correctly. After 50 valid trials, the display shows the total number of errors (initial movement toward the target).

2. Data Acquisition Mode:

In data acquisition mode, the sequence of cues is controlled by a host PC connected through a serial-port cable (RS232). The microprocessor digitizes and records eye movement continuously for a preset block of time and then uploads the data buffer to the host PC, which performs any data analysis. This enables a researcher to design more complex behavioural paradigms and to take advantage of the additional cue-generating capabilities in the helmet. These include different color lights in the central and lateral target positions and built-in headphones that can generate clicks, buzzes and tones to either or both ears. It is also possible to create and download new paradigms for stand-alone operation through this interface.

Background

Attention-deficit hyperactivity disorder (ADHD) is a disability affecting approximately 5% of all school-aged children. The core symptoms include impulsivity, hyperactivity and inattentiveness. These symptoms often lead to behavioural difficulties in the classroom. The symptoms are chronic and these children must develop strategies to help them cope with their life-long disability.

Until now, the diagnosis of ADHD depended on several behavioural and psychological evaluations that were prone to subjective biases. These limitations have been successfully overcome through the use of eye movement recording during various oculomotor paradigms.

Illustration of Visual Stimuli

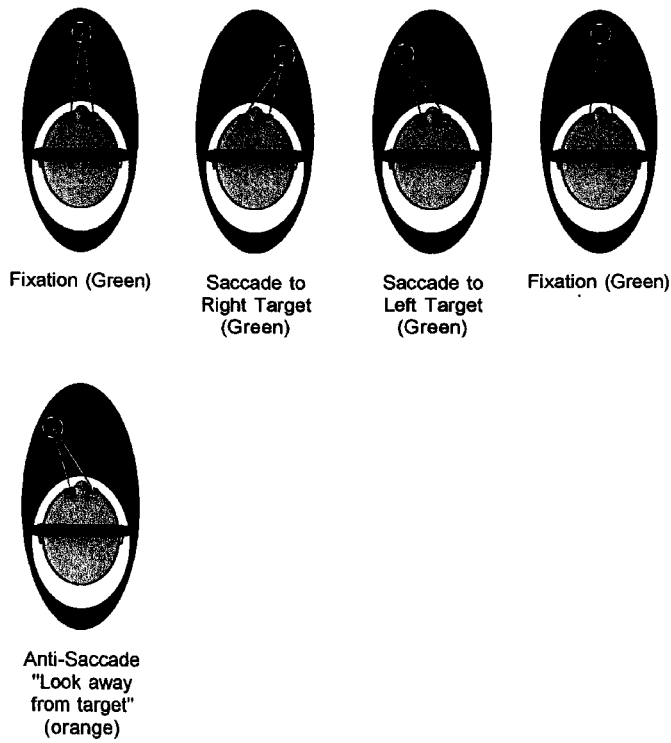

Fixation (Green)  Saccade to Right Target (Green)  Saccade to Left Target (Green)  Fixation (Green)

Anti-Saccade "Look away from target" (orange)

*Basic Procedures*

1) Prepare the skin surface by cleaning with isopropyl alcohol.
2) Apply electrodes (as shown on page 5).
3) Attach "clip leads" to electrodes.
4) Place helmet on subject.
5) Adjust helmet for comfort ensuring there is good contact between the skin and ground, located on the band resting on the forehead.
6) Plug electrode leads into jacks.
7) Instruct subject about calibration procedure.
8) Start Calibration mode by pushing Start/Reset button once.
9) LCD on back of helmet displays CC to identify the start of Calibration mode, then pauses at the end of calibration displaying 00 on the LCD. (If a calibration error occurs, the calibration must be repeated until LCD displays 00.)
10) Instruct subject about task.
11) Start Task mode by pushing Start/Reset button once.
12) After Task mode is complete, subject's score will be displayed on LCD as the number of initial errors out of 50 valid trials.
13) Task mode can be rerun without calibration by simply pushing Start/Reset once.

- Either mode can be interrupted by pressing the Start/Reset button once, which will cause the helmet to revert to calibration mode.
- If the helmet is not given any Start input for two minutes, it automatically shuts off power, losing the display. The next Start/Reset will revert to calibration mode.

Special Considerations for EOG recordings

Proper electrode placement is essential for the HyperSpace Helmet™ to function effectively. Special care should be taken to make sure that the application site is clean and dry. Any hair, dirt or skin blemishes underneath the electrode may cause incorrect readings or the helmet to not function at all. Extra time spent on applying the electrodes will produce fewer errors and less frustration.

One electrode should be placed at the lateral margin of each eye. The tab on the electrode (see illustration below and on page 9) should point downwards to allow electrode cables to attach easily on bottom side of electrode.

When placing helmet over the head, be sure to avoid displacing clip leads, by loosening the adjusting strap on the back of the head.

It may be advisable to dark adapt the subject inside the helmet for some time (~2 minutes) before starting any procedures. It is important to reassure young children that someone is there at all times.

Do not allow gum chewing as this will dislodge electrodes and cause electrical instability.

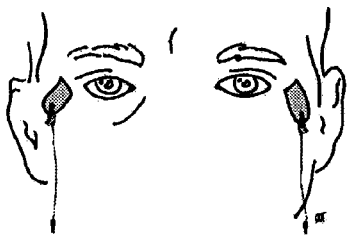

*Program Outline*

Calibration mode is entered by pushing the Start/Reset button once. Instruct subject to look at each green light in turn before pressing Start/Reset.

LCD Display:

Calibration Mode   *(viewed from rear)*

1) System power on with 1.0 second delay before task. ——————
2) Centre LED is illuminated. ——————————————
3) Subject focuses on centre LED and eye position is recorded. ——————
4) Right LED is illuminated. ——————————————
5) Subject focuses on right LED and eye position is recorded. ——————
6) Left LED is illuminated. ——————————————
7) Subject focuses on left LED and eye position is recorded. ——————
8) Centre LED is illuminated. ——————————————
9) Subject focuses on centre LED and eye position is confirmed. ——————
10) LCD display shows 00 ——————————————————— `[00]`

Or LCD display shows one of the following Calibration Errors:
   EOG unstable ———————————————— `[E1]`
      *-check loose wires, improve skin prep*
   EOG too small ———————————————— `[E2]`
      *-place closer to eyes, improve skin prep*
   EOG saturated ———————————————— `[E3]`
      *-place further from eyes*

- Pressing Start/Reset during calibration restarts Calibration Mode.
- It is impossible to bypass Calibration Mode until calibration 00 is achieved.

*Program Outline*

Task mode can be entered by pushing the Start/Reset button only after a valid calibration. Instruct subject about anti-saccade task before pushing Start/Reset.

LCD Display:

Task Mode  *(viewed from rear)*

1) System power on with 1.0 second delay before task.  ———— `00`
2) Centre LED is illuminated.  ————————————————
3) Subject focuses on centre LED and eye position is confirmed.  ————
   *(Centre position is sampled, and recentred)*
4) Start data buffer. Turn all LED's off for 0.2s.  —————————

Direction of light
Direction of Initial Saccade
Direction of second corrective saccade 5) Random target LED is illuminated.  —————

6) Saccades are recorded and displayed:
   a) Correct Response  ——————————
   b) Initial Error  ———————————
   c) Initial Error with Correction  ———
   d) Misunderstood task (not counted)
      Hold in this state until subject
      makes correct antisaccade 7) Antisaccade task will repeat for 50 valid trials or until a terminal error.
8) After 50 trials, display shows total number of Initial errors.  ———— `25`

- A single press on Start/Reset within 2 minutes will run another set of 50 task trials.
- Pressing Start/Reset again during task reverts to calibration mode.

Terminal Error Codes a) Greater than 5 trial restarts due to "No eye movement detected"  ————
b) Greater than 10 trial restarts due to "Misunderstood trials detected"  ————
c) Greater than 10 trial restarts due to "Loss of Fixation"  ————————  `LF`
   (subject fails to maintain gaze)

Design Manual

*Breakdown of Program Outline*

High Level Task Sequencing

Refer to:

High Level Task Sequencing Flow Chart. (appendix I)

This chart outlines the basic sequence of events occurring from powering on the helmet to completion of the task including re-initiation of the sequence due to various errors.

- After verbal instructions are given to the subject, one press of the Start/Reset button begins the Calibration Mode.
- During the calibration, one touch of the Start/Reset button again will simply begin the calibration again. It is impossible to move into Task Mode without obtaining a valid calibration (indicated by a 00 on the LCD display).
- Verbal instructions are then given to the subject regarding the task and one press of the Start/Reset button initiates the Task Mode (collection of 50 valid trials).
- During the task, if the Start/Reset button is pressed, another calibration must be performed.
- Upon completion of the task, the score is noted and the task can either be repeated by pressing the Start/Reset button or the helmet can be removed.
- If the Task Mode is not re-initiated within 2 minutes, the helmet will automatically power off and the entire sequence must begin again from the top.
- Errors can also cause the helmet to reset to the beginning. Please see page 6 for a description of Calibration Mode errors or page 7 for Task Mode errors.

Calibration Mode

Refer to:

Calibration Mode Timing Diagram (appendix II)

Calibration Mode Flowchart (appendices III and IV)

Task Mode

Refer to:

Task Mode Timing Diagram (appendix V)

Task Mode Flowchart (appendix VI)

Electrode Application and Signal Amplification

Once the electrodes are properly attached to the subject, the electrode wires can be attached to the electrodes. The HyperSpace Helmet™ is equipped with pin jacks to accept the "pin" end of the electrode wires. The pin jacks are located inside the helmet's shell just in front of the built in ear speakers. The "pin" of the electrode wire pushes into the jack mounted on the helmet to provide a solid connection.

Two silver/silver chloride electrodes attached to the subject acquire a dc potential signal at about 1mV. An instrumentation amplifier is used to amplify the raw signal from the subject. A second amplifier stage is used to amplify and filter the signal from the preamplifier. The amplified EOG signal has a maximal potential of +5 volt for an eye movement in the right direction and –5 volts for an eye movement in the left direction.

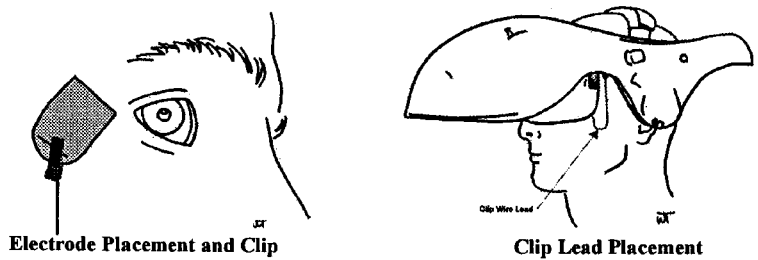

Electrode Placement and Clip           Clip Lead Placement

LED Illumination (Centre, and Targets)

The tricolor LEDs (RED, GREEN, and ORANGE), are illuminated via ports on the microcontroller. Two port pins are used for each LED, yielding a total of 6 port pins for 3 LEDs. A buffer is placed between the microcontroller port pins and the LED's to reduce the current load on the microcontroller. Maximal LED intensity is controlled mainly through hardware wiring of resistor values, although it is possible to decrease the intensity of each LED by modulating the port pins.

Digitization of EOG Signal

Amplified EOG signals are digitized at 500 samples per second. The A-D notifies the microcontroller, using a port pin, when a digitized sample is ready to be stored in the memory. As one sample is digitized, the microcontroller stores the previously digitized sample. Data storage only occurs during a paradigm.

*Liquid Crystal Display*

The display mounted on the outside of the helmet provides the following operator feedback:
a) Indicates that "helmet" is turned on.
b) Displays Calibration Mode or Task Mode indicator.
c) Provides program feedback to operator during run time.
d) Alerts operator to problems with operation.
e) Provides end of paradigm quick analysis.

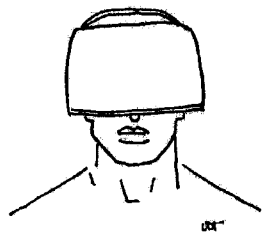

*Power Supply*

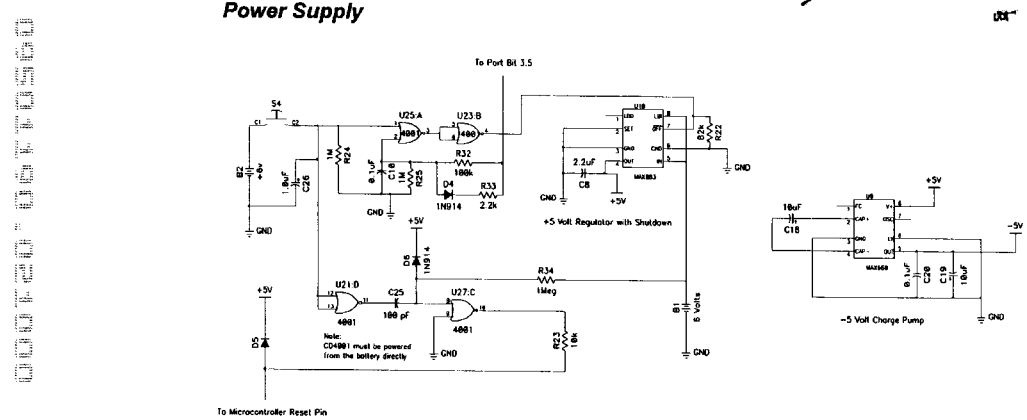

Four 'AA' batteries produce a six volt primary supply. The Maxim MAX883 is a +5 volt regulator with shutdown. It supplies +5 volts to the entire circuit board. The MAX883 can be shutdown by the microcontroller using port pin 3.5. Shutting down the regulator removes power to most of the circuits components and effectively turns the helmet off when it is not in use to conserve power. The one component that remains powered directly from the battery source is the CD4001. This component requires power at all times in order for on/off switch operation. Negative 5 volts is supplied for the amplifier and analog to digital converter by the MAX660 charge pump. Current drawn by the electronics when the helmet is off is 0.428mA. 21.6mA are drawn when the helmet is on.

The Helmet

The HyperSpace Helmet™ is a highly modified virtual reality device. The helmet is fully adjustable and should be comfortable for a range of subjects. By shielding the eyes from ambient light, the subject should be able to focus on the task without outside distractions. In stand-alone operation, the helmet is free of any exterior cables, and operates entirely on its own battery pack, maintaining high portability of the device.

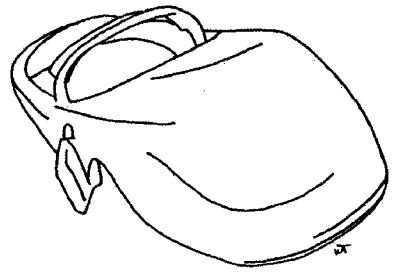

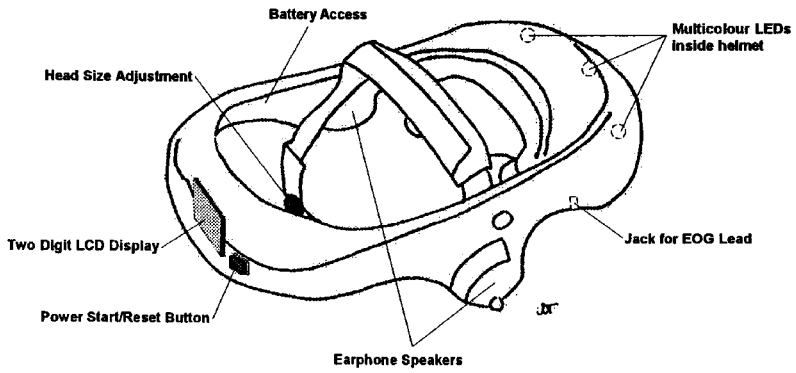

List of Components

Major:
⇒ helmet

Accessories:
⇒ 4 AA batteries
⇒ electrodes
⇒ 2 electrode connector wires

Optional:
⇒ serial cable

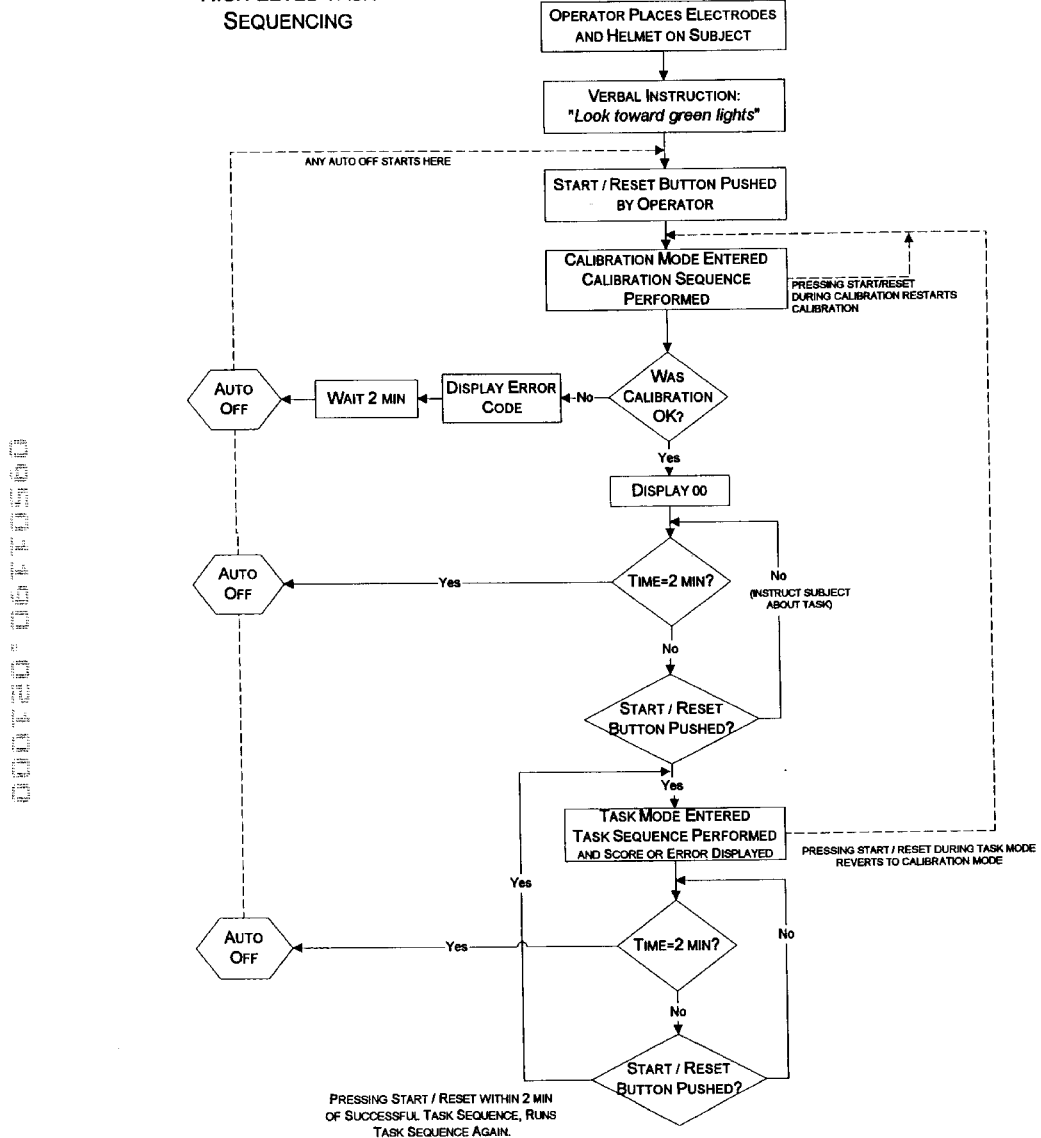

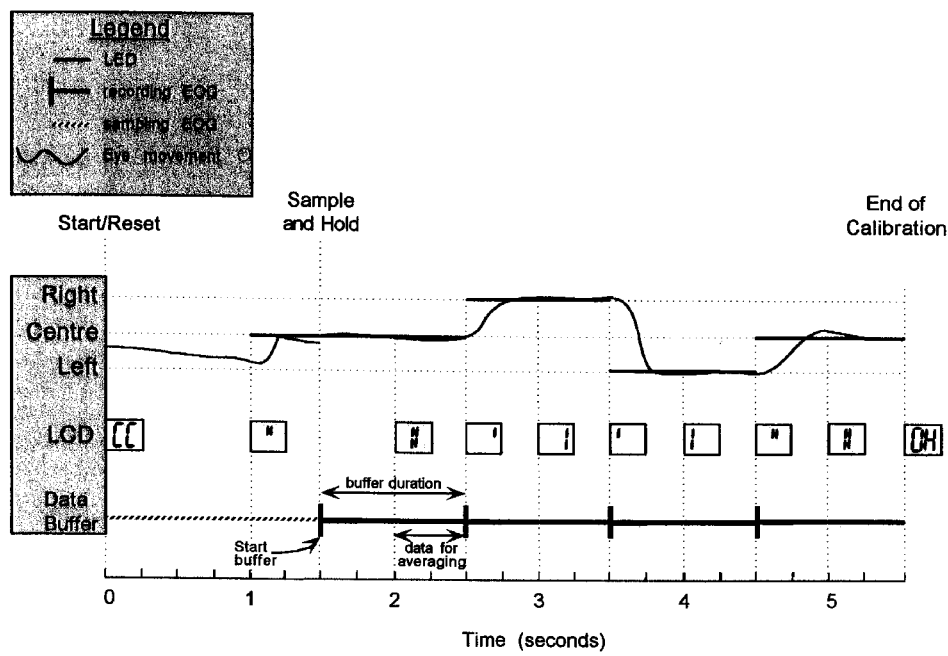
APPENDIX II
CALIBRATION MODE TIMING DIAGRAM

Appendix III (a)
CALIBRATION MODE FLOWCHART
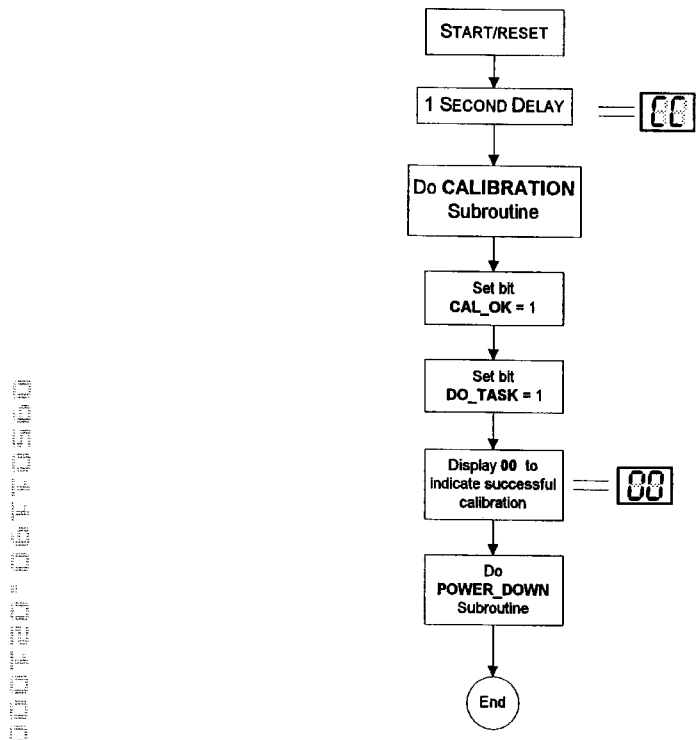

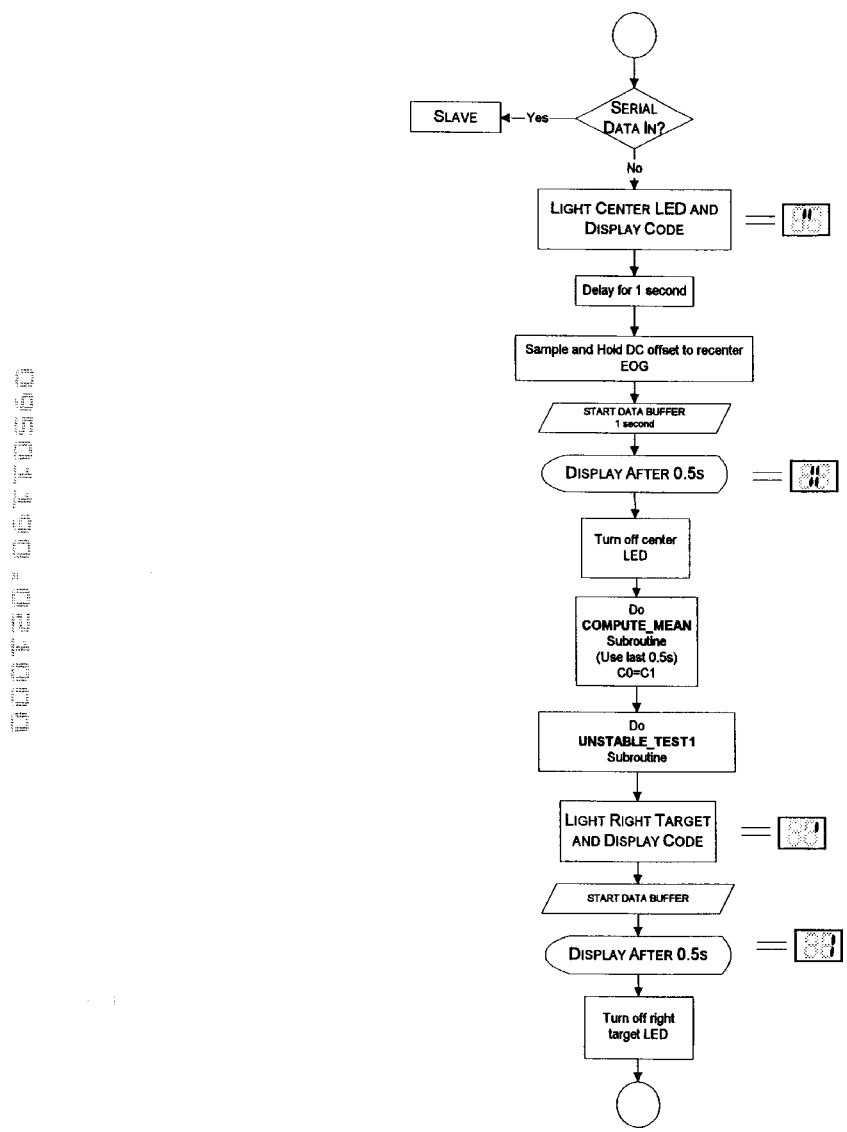

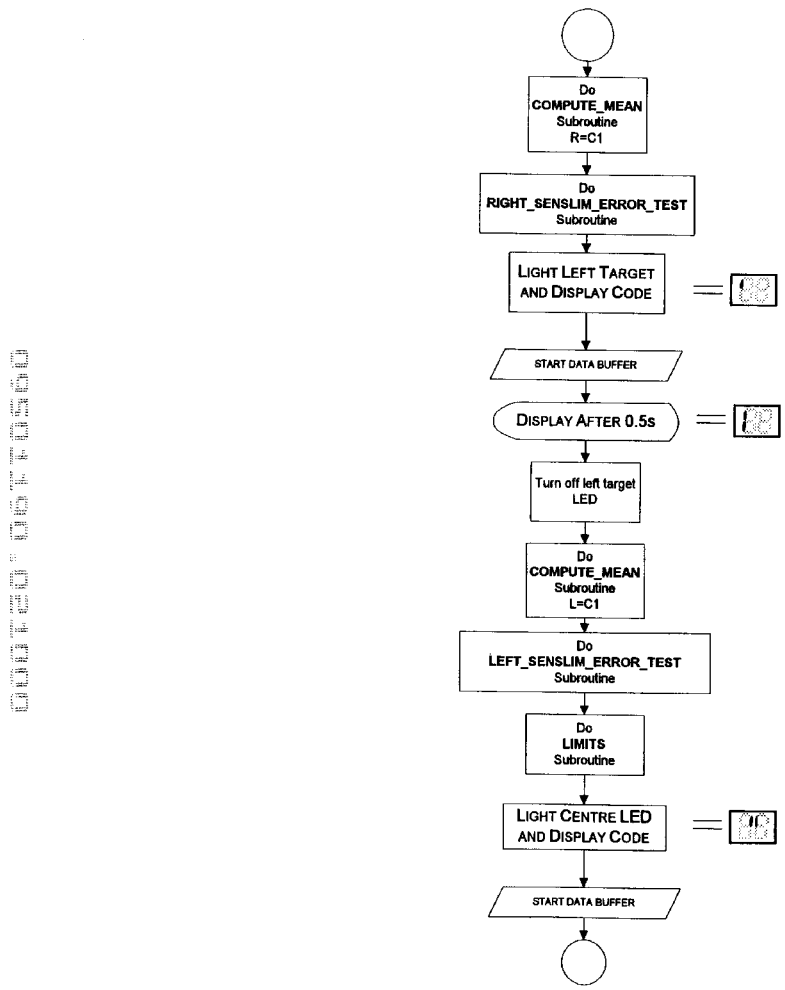

Appendix III (b3)
CALIBRATION SUBROUTINE
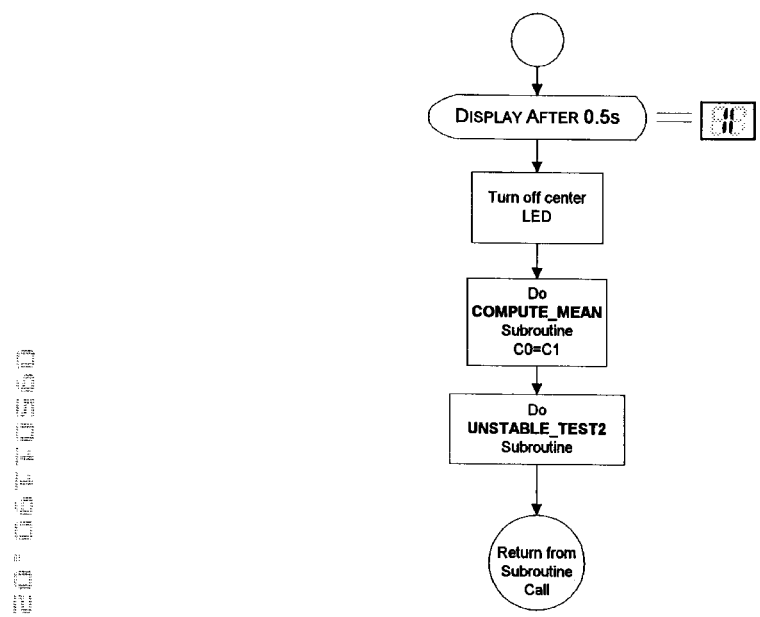

Appendix III (c)
COMPUTE_MEAN SUBROUTINE
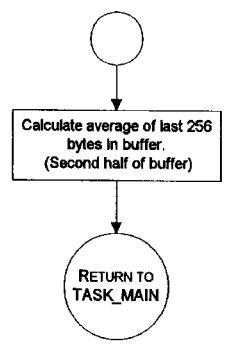

Appendix III (d)
UNSTABLE_TEST1 SUBROUTINE
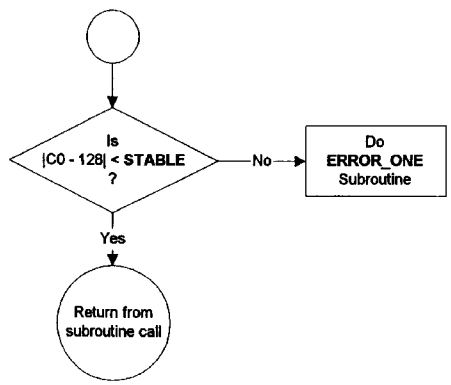

Appendix III (e)
RIGHT_SENSLIM_ERROR_TEST SUBROUTINE
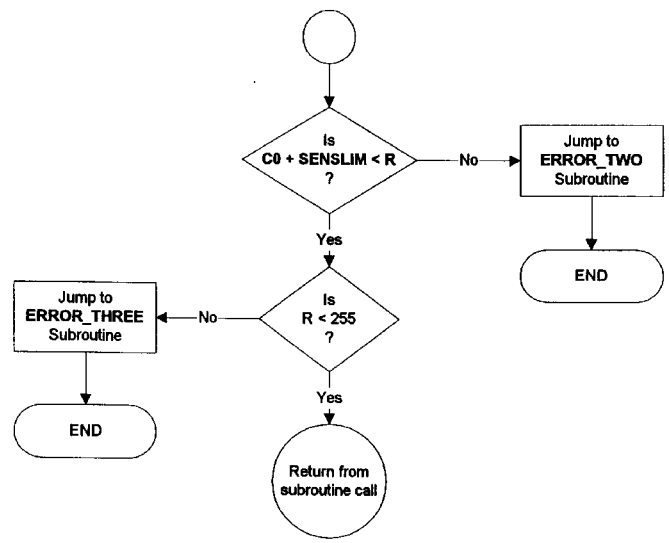

Appendix III (f)
LEFT_SENSLIM_ERROR_TEST SUBROUTINE
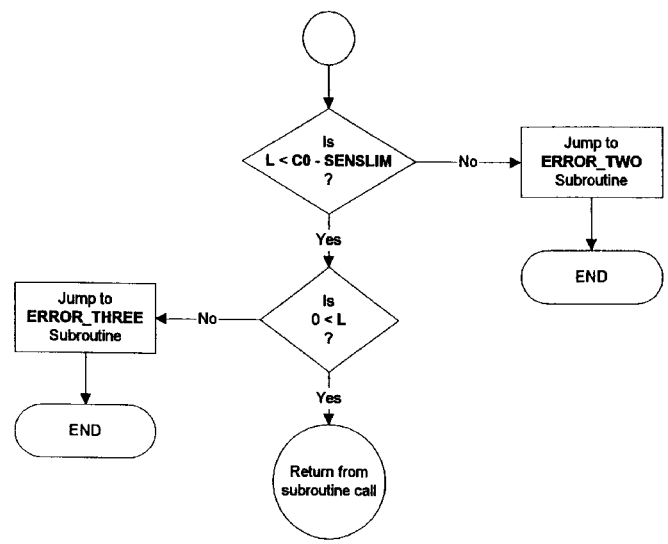

Appendix III (g)
LIMITS SUBROUTINE
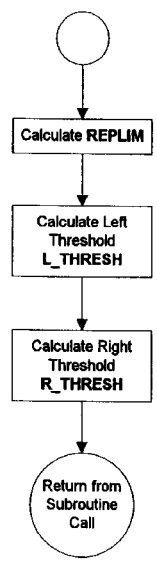

Appendix III (h)
UNSTABLE_TEST2 SUBROUTINE
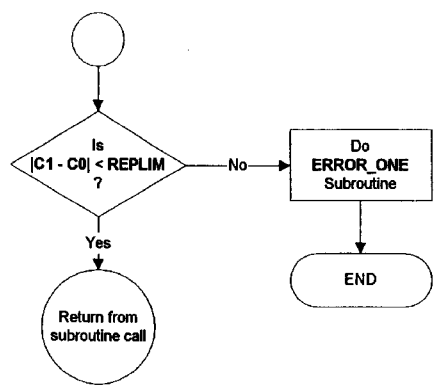

Appendix III (i)
ERROR_ONE SUBROUTINE
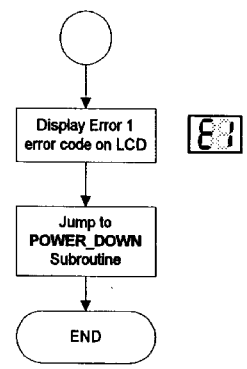

Appendix III (j)
Error_Two Subroutine
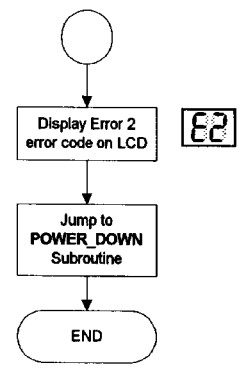

Appendix III (k)
ERROR_THREE SUBROUTINE
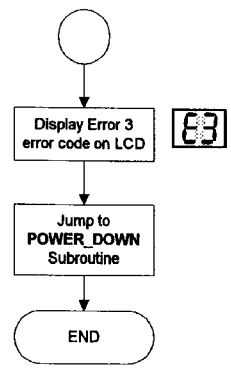

APPENDIX IV

CALIBRATION MODE CALCULATION DIAGRAM
*(Sample Calculations)*

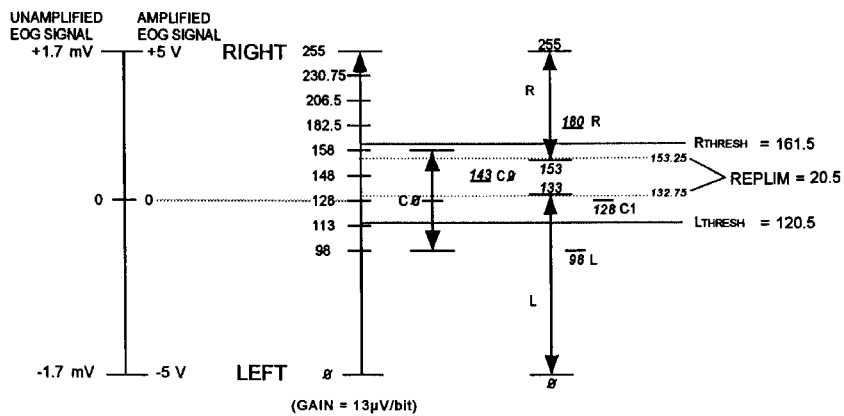

(GAIN = 13μV/bit)

DATA
AVERAGES

| | | |
|---|---|---|
| C0 | \|C0 - 128\| >STABLE | (SENSLIM=10) |
| R | C0 + SENSLIM<R<255 | (STABLE=50) |
| L | 0<L<C0 - SENSLIM | |
| C1 | \|C1 - C0\|<REPLIM | |

$$REPLIM = \frac{R-L}{4} = \frac{180-98}{4}$$

$$LTHRESH = C0 - \frac{C0-L}{2} = 143 - \frac{143-98}{2}$$

$$RTHRESH = \frac{R-C0}{2} + C0 = \frac{180-143}{2} + 143$$

LEGEND:

SENSLIM - sensitivity limit
REPLIM - repeat limit
LTHRESH - left threshold
RTHRESH - right threshold Reproducibility error of center position (C1-C0) should be less than 1/4 of the range between right and left eye positions. Each threshold is halfway between center and and eye position when looking in that direction.

44

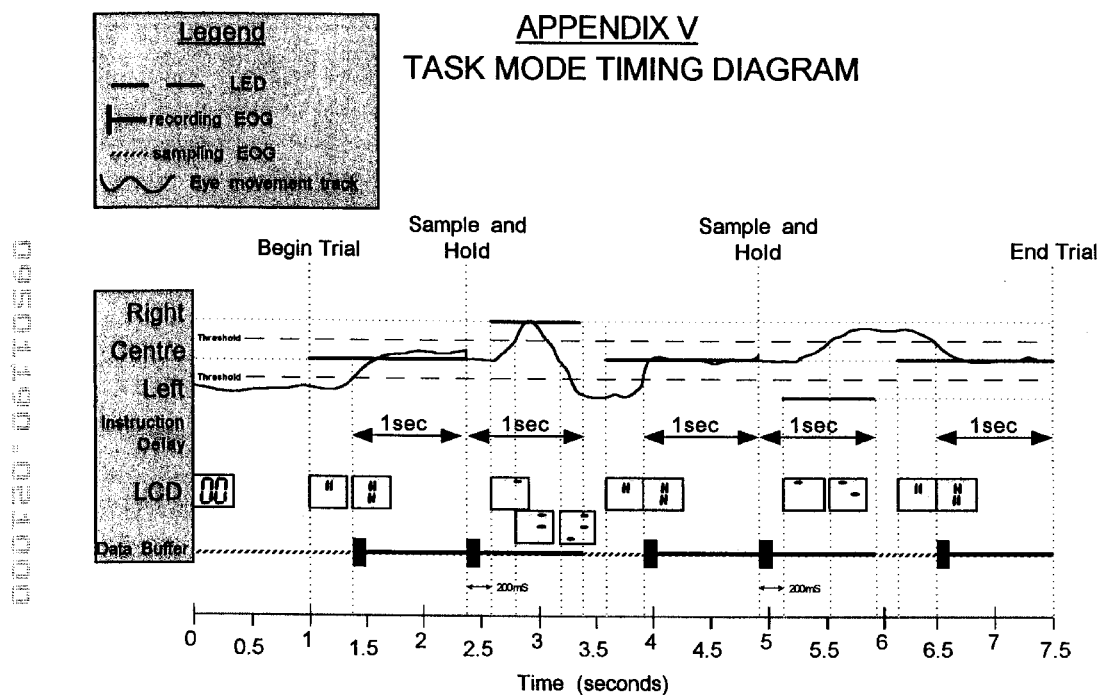

Appendix VI (a)
TASK MODE FLOW CHART
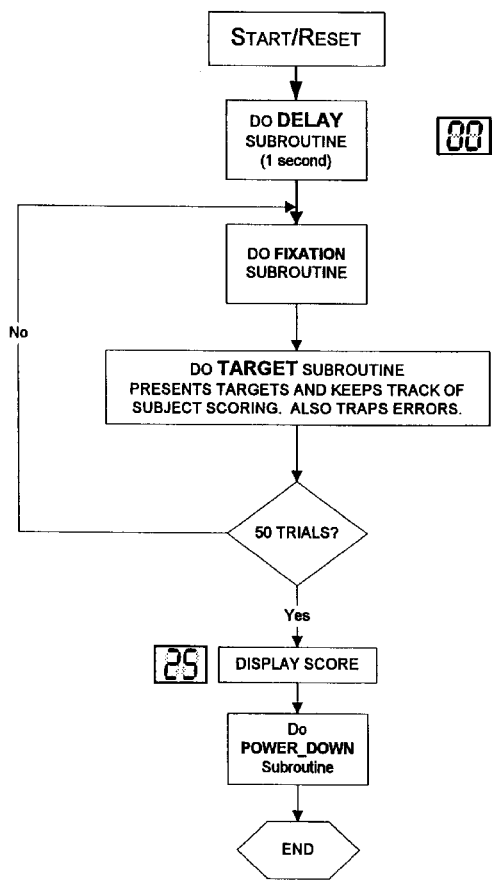

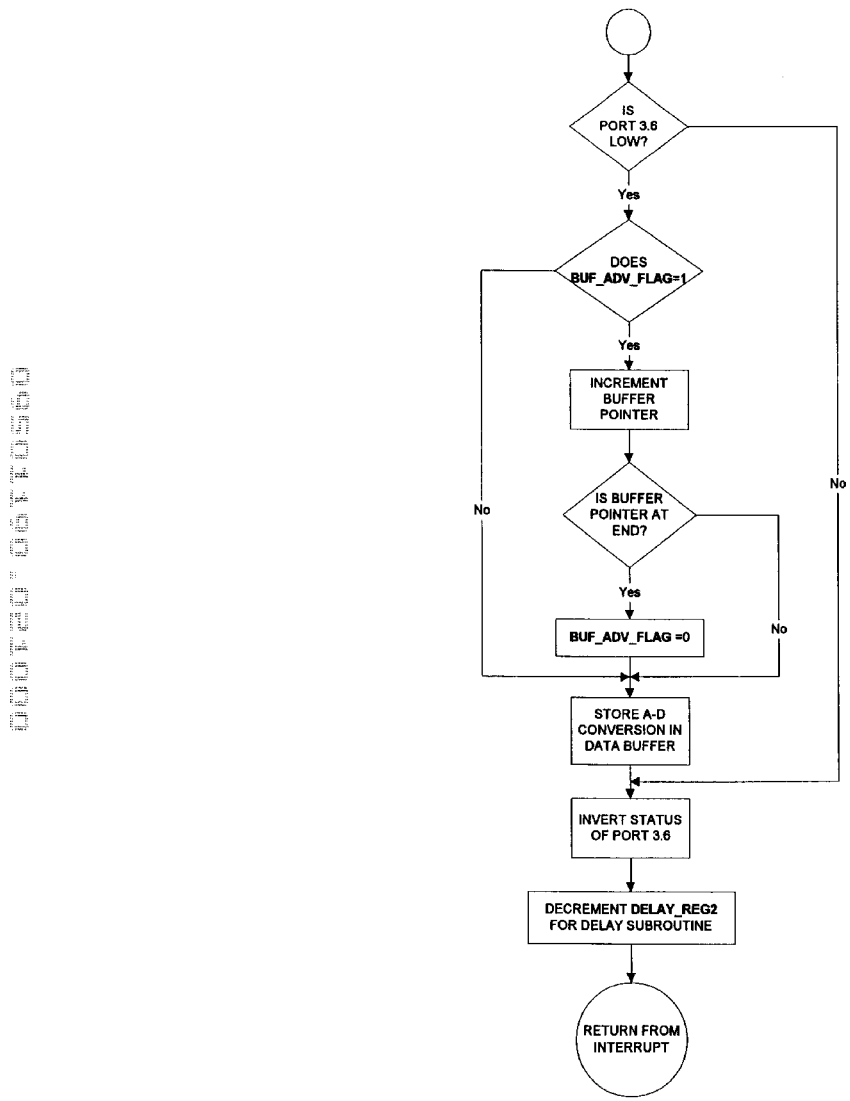

Appendix VI (c)
SERIAL SUBROUTINE
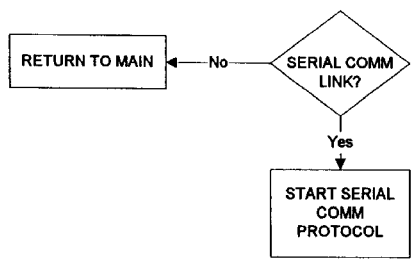

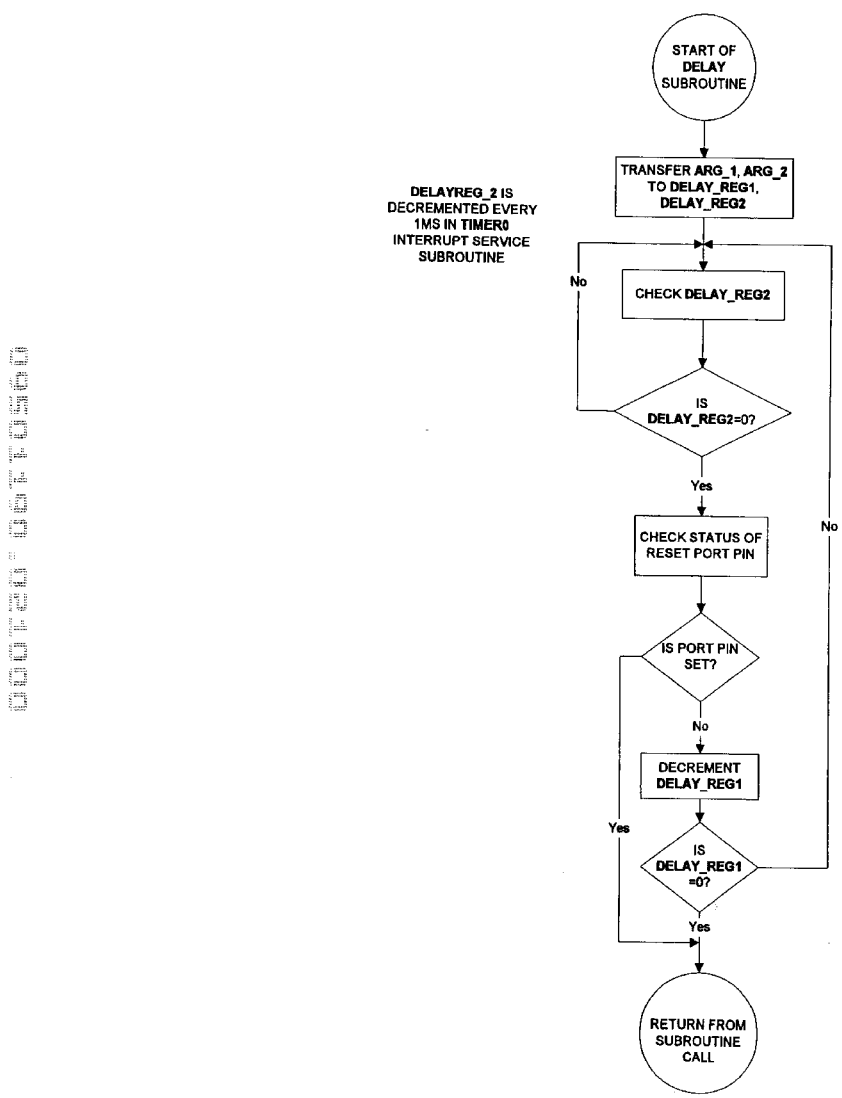

Appendix VI (e)
FIXATION SUBROUTINE
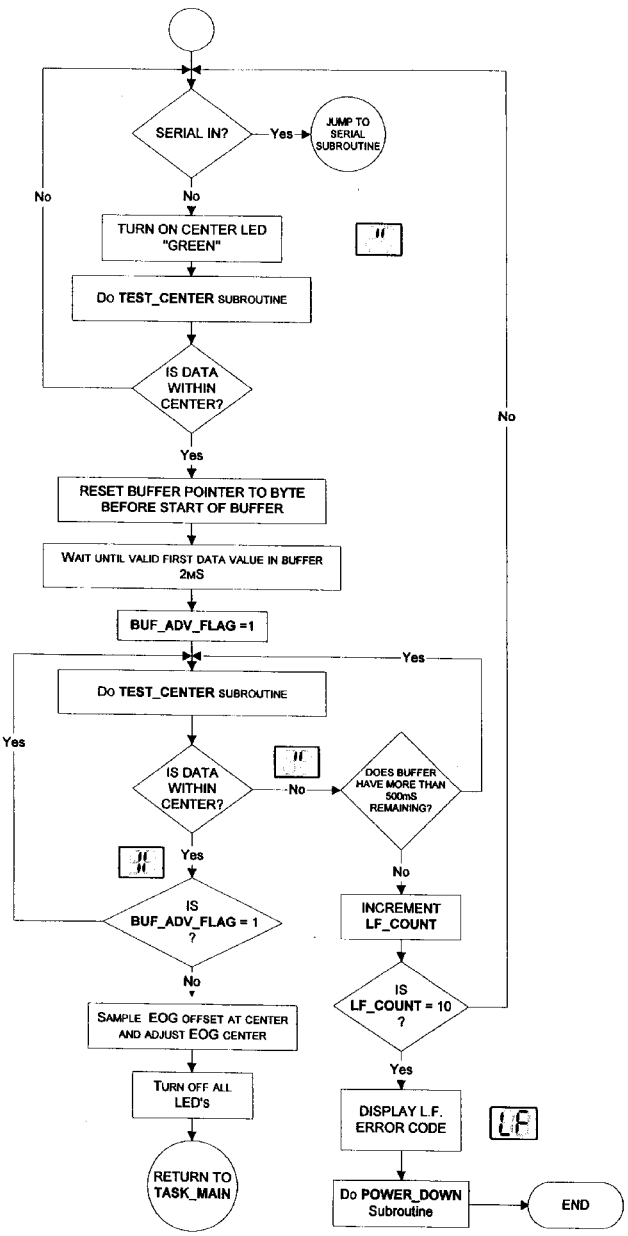

Appendix VI (f)
TEST_CENTER SUBROUTINE
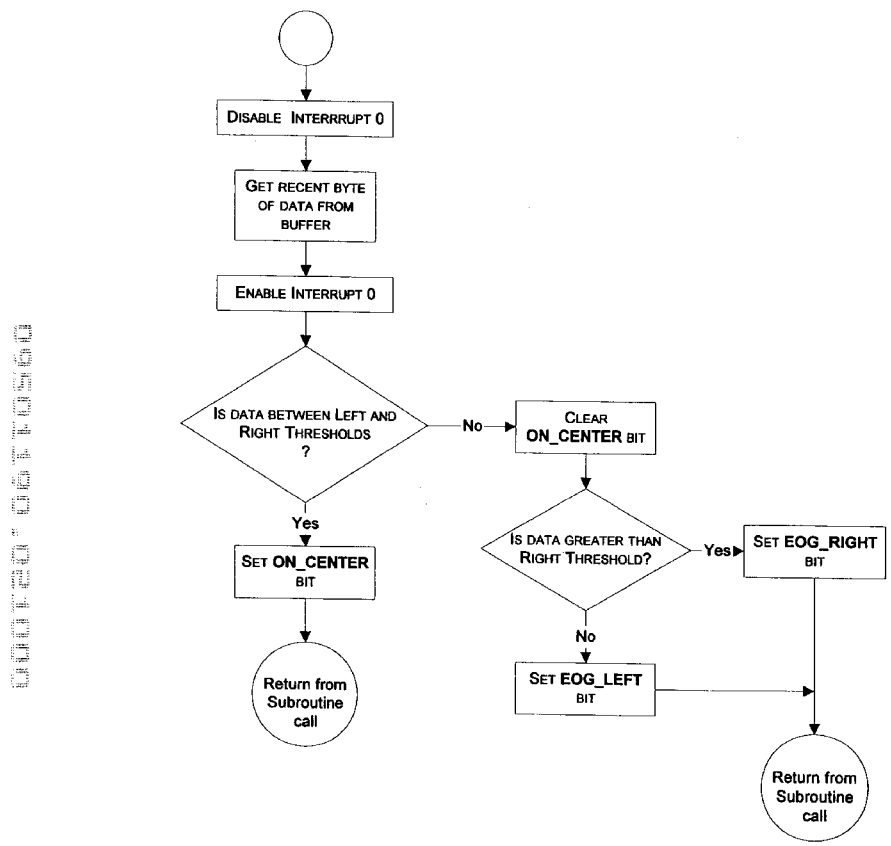

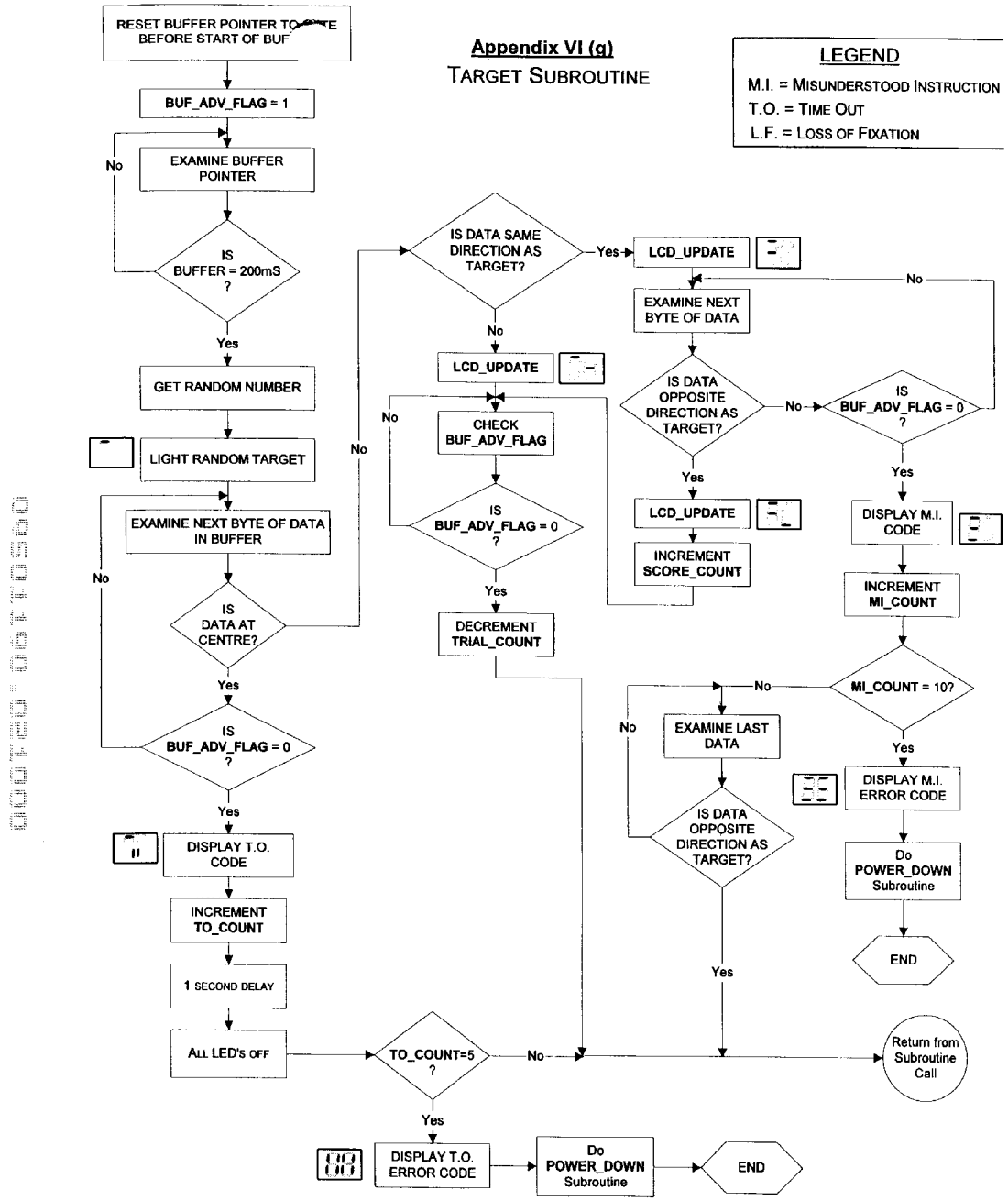

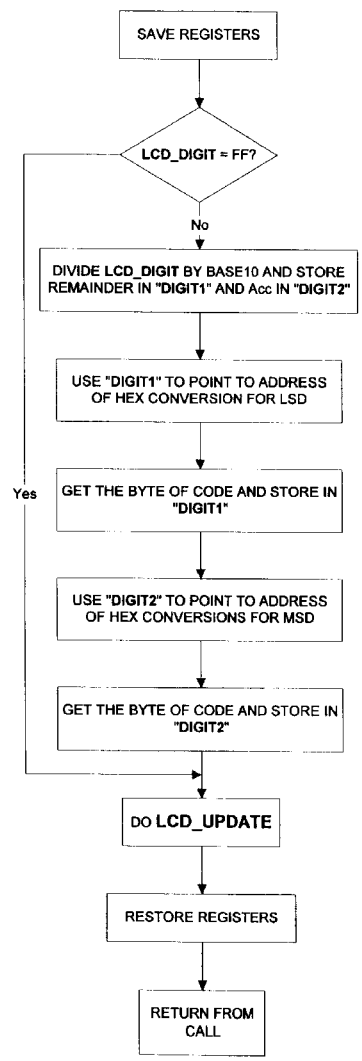

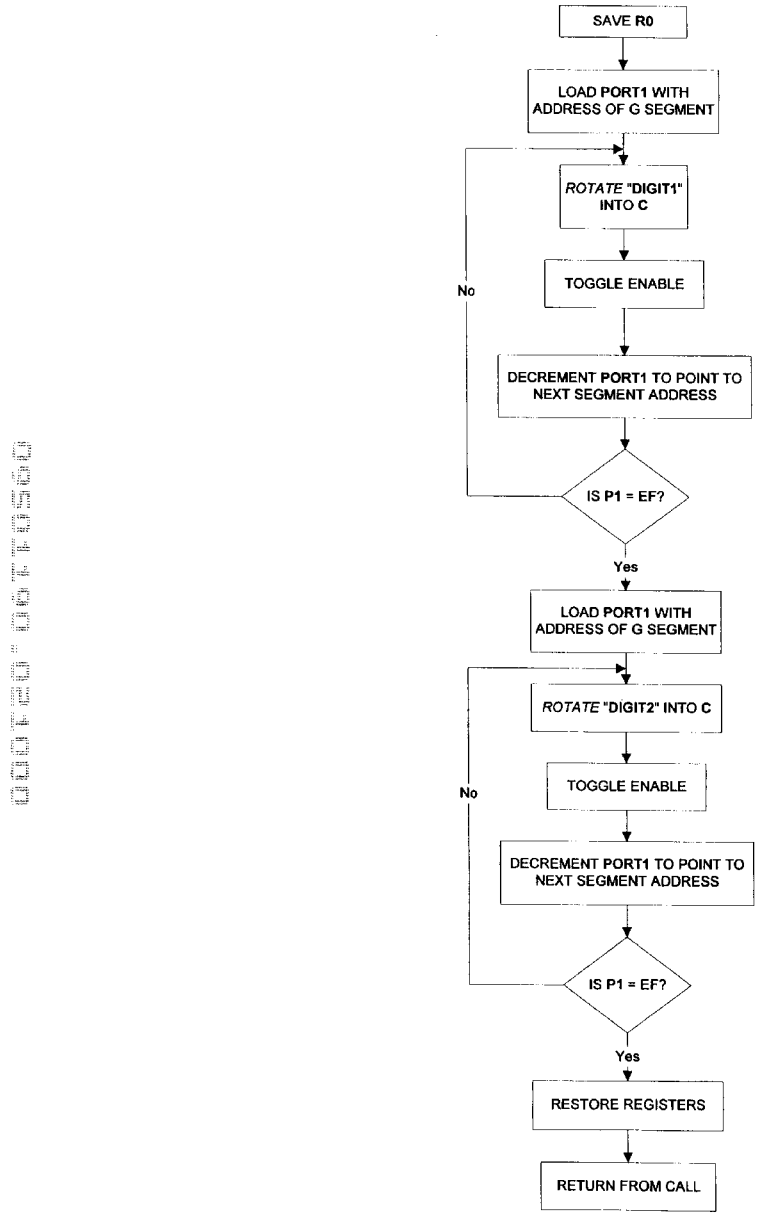

APPENDIX VII

Dallas DS5000T 32-8 Memory Map

In the DS5000, all of the program/data space is provided in a single memory chip (SRAM). The division between program space and data space is called the PARTITION. Memory size is referred to as RANGE and can be either 8KB or 32KB. The rotating buffer occupies the top 1KB of data memory. Program memory originates at address 0100h to allow room for interrupt vector addresses at start of memory block. Data storage space occupies available memory space between the rotating buffer and program memory (Partition address). The amount of space allocated for data storage is dependant upon the size of program memory (ie. location of partition address) and the size of memory in DS5000 (8KB or 32KB).

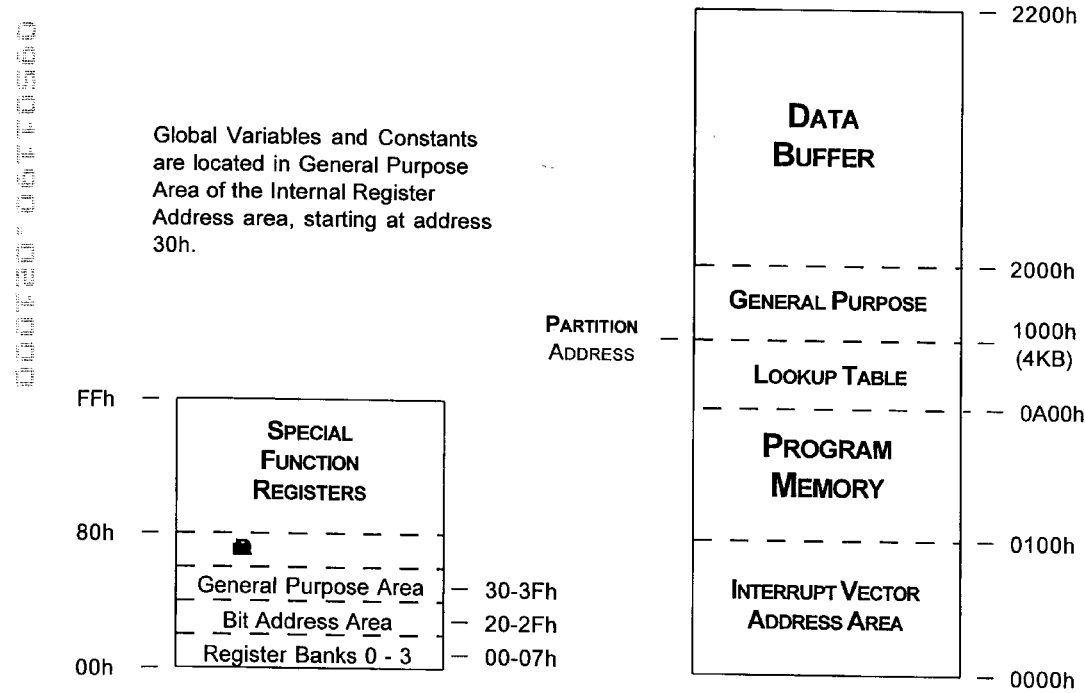

Data memory is accessed using both MOVX and MOVC commahds, due to the fact that ROM and RAM are essentially the same due to the internal nonvolatile SRAM of the DS5000.

APPENDIX VIII

HyperSpace Helmet™
8051 Master Port Pin Listing

|        | Pin 0 | Pin 1 | Pin 2 | Pin 3 | Pin 4 | Pin 5 | Pin 6 | Pin 7 |
|--------|-------|-------|-------|-------|-------|-------|-------|-------|
| Port 0 | A/D D0 Pin 15 | A/D D1 Pin 14 | A/D D2 Pin 13 | A/D D3 Pin 12 | A/D D4 Pin 11 | A/D D5 Pin 9 | A/D D6 Pin 8 | A/D D7 Pin 7 |
| Port 1 | 74259 A0 Pin 1 | 74259 A1 Pin 2 | 74259 A2 Pin 3 | 74259 D Pin 13 | 74259 $MR_1$ Pin 15 | 74259 $En_1$ Pin 14 | 74259 $MR_2$ Pin 15 | 74259 $En_2$ Pin 14 |
| Port 2 | Speaker 1 | Speaker 2 | 7404 Pin 1 Center Red | 7404 Pin 9 Right Green | 7404 Pin 3 Right Red | 7404 Pin 11 Left Green | 7404 Pin 5 Left Red | 7404 Pin 13 Center Green |
| Port 3 | Max 220 Rx Pin 9 | Max 220 Tx Pin 10 | CD4001 Sample and Hold | N/C | Max 166 CLK Pin 6 | MAX 883 shutdown pin | MAX 166 CS & RD Pins 1 & 2 | |

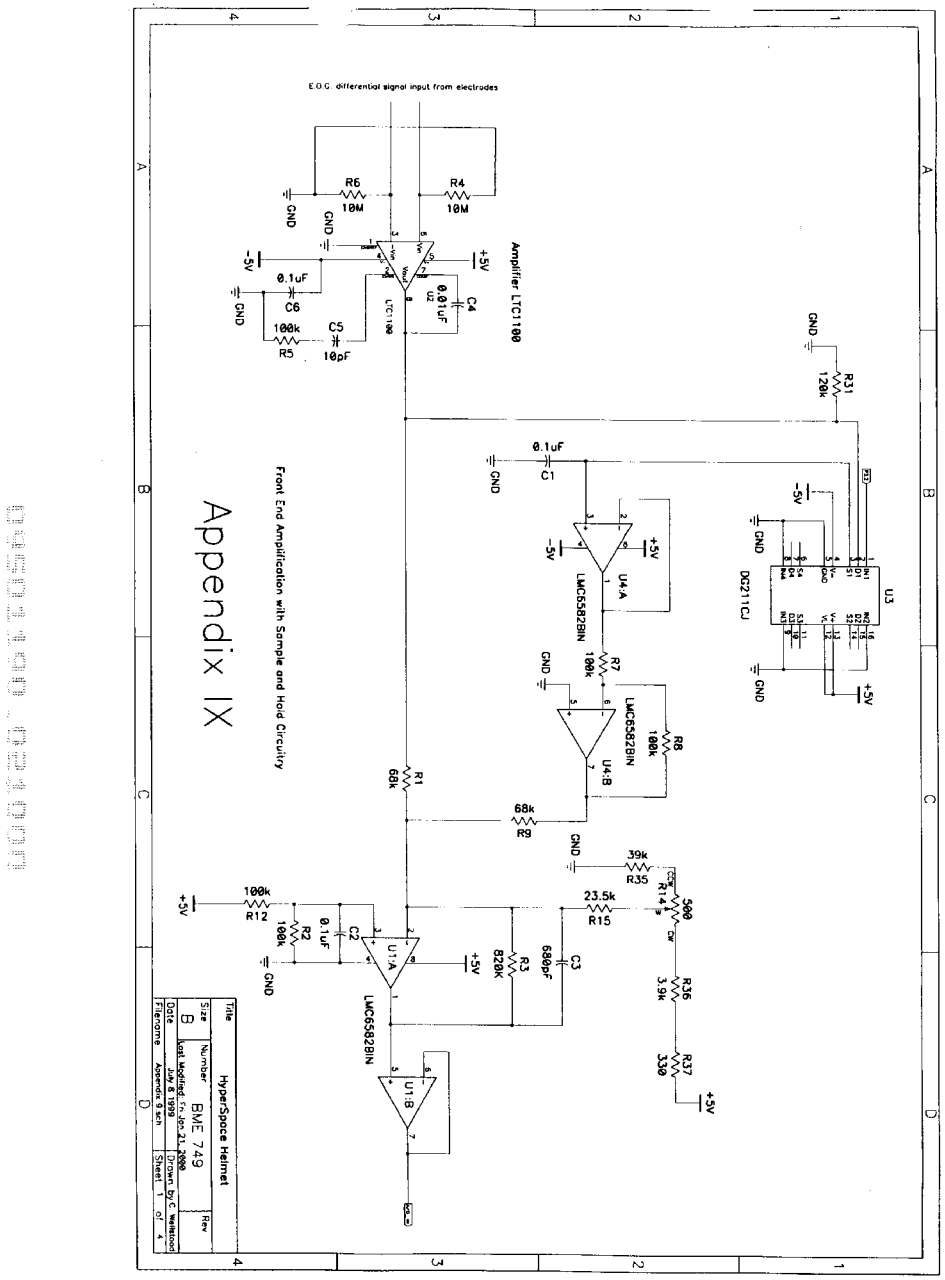

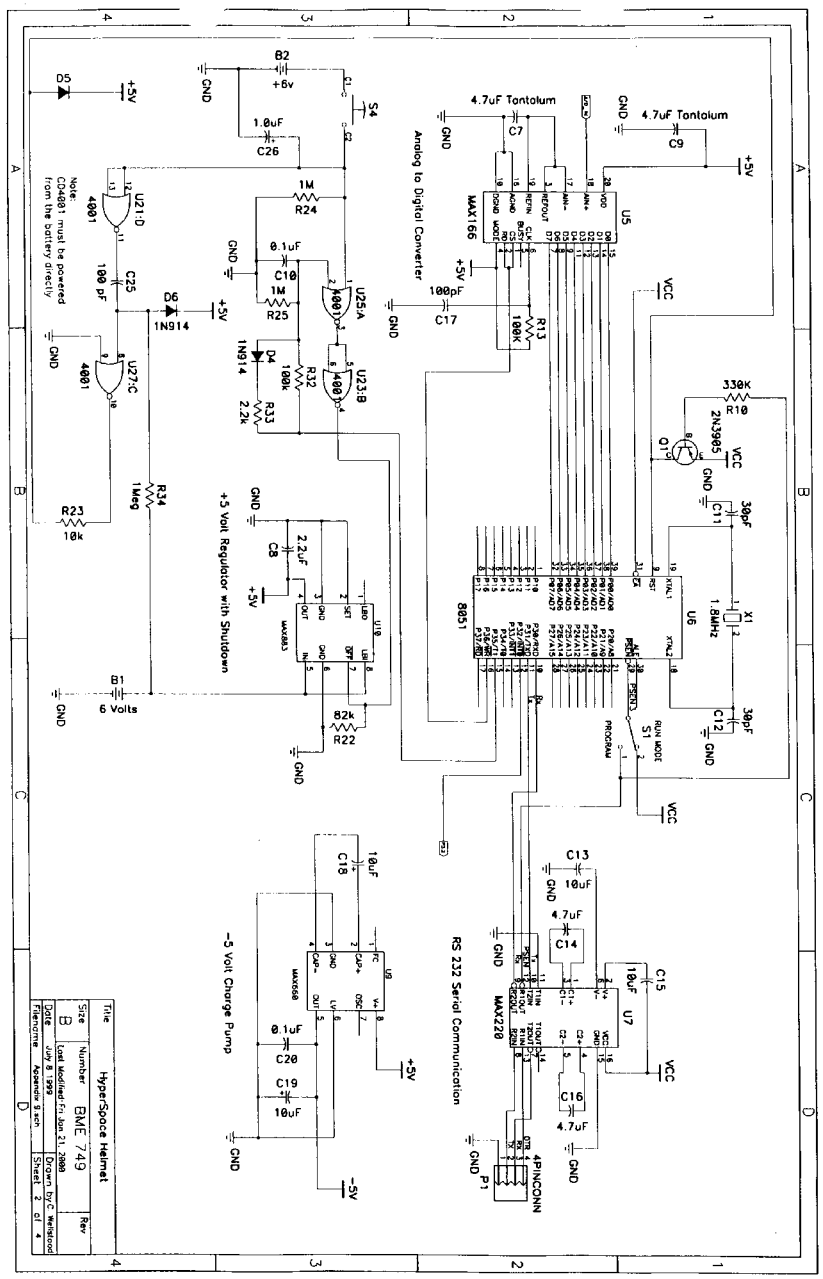

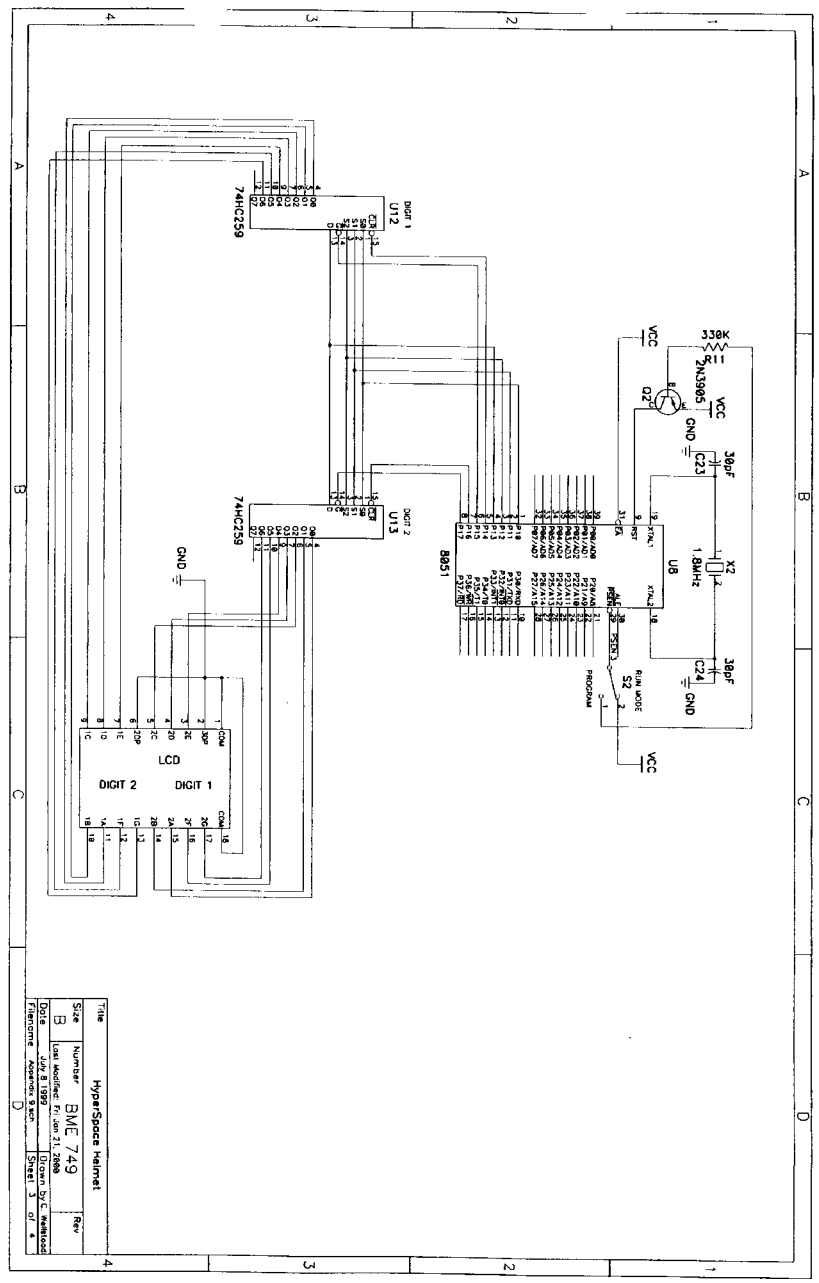

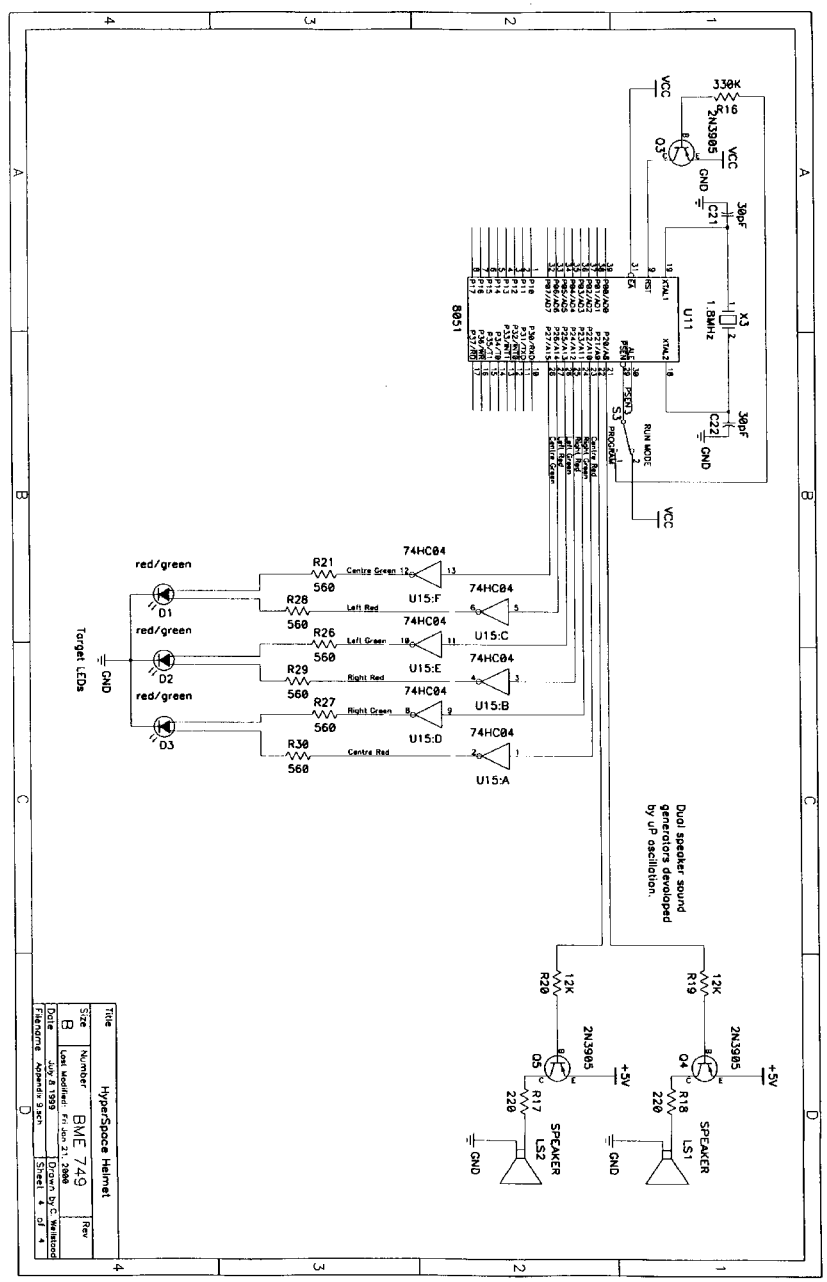

Appendix X
LCD Digit
Segment Select Table
| 8051 pins | P1.7 | P1.6 | P1.5 | P1.4 | P1.3 | P1.2 | P1.1 | P1.0 | HEX# |
|---|---|---|---|---|---|---|---|---|---|
| LCD Segment / 74259 pins | $En_2$ Pin 14 | $MR_2$ Pin 16 | $En_1$ Pin 14 | $MR_1$ Pin 15 | D? | $A_2$ Pin 3 | $A_1$ Pin 2 | $A_0$ Pin 1 | |
| A | 1 | 1 | 1 | 1 | 1 | 0 | 0 | 0 | F8 |
| B | 1 | 1 | 1 | 1 | 1 | 0 | 0 | 1 | F9 |
| C | 1 | 1 | 1 | 1 | 1 | 0 | 1 | 0 | FA |
| D | 1 | 1 | 1 | 1 | 1 | 0 | 1 | 1 | FB |
| E | 1 | 1 | 1 | 1 | 1 | 1 | 0 | 0 | FC |
| F | 1 | 1 | 1 | 1 | 1 | 1 | 0 | 1 | FD |
| G | 1 | 1 | 1 | 1 | 1 | 1 | 1 | 0 | FE |
74HC259
| Operating Mode | MR | E |
|---|---|---|
| Master Reset | Low | High |
| Store | High | High |
| Addressable Latch | High | Low |
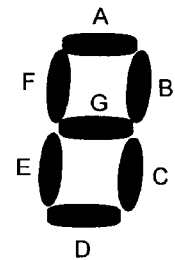
LOOKUP TABLE OF SPECIAL LCD CODES
| 0 | 1 | 2 | 3 | 4 | 5 | 6 | 7 | 8 | 9 | A | B | C | D | E | F |
|---|---|---|---|---|---|---|---|---|---|---|---|---|---|---|---|
| 0 | 1 | 2 | 3 | 4 | 5 | 6 | 7 | 8 | 9 | L | = | C | i | E | F |
VIEWER'S LEFT (SUBJECT'S LEFT) — DIGIT 1 DIGIT 2 : 00

We claim:

1. An apparatus for diagnosing a neurological disorder in a subject by detecting the subject's eye movement, comprising:
   a helmet for blocking visual stimuli from the subject's visual field;
   at least one visual cue disposed inside the helmet within the visual field of the subject when the helmet is placed on the subject's head, the visual cue capable of being switched from on to off states;
   at least two electrodes for attaching to the subject's head, the electrodes producing electrical signals corresponding to the subject's eye movements;
   signal processing means for controlling on and off states of the visual cues, receiving and processing electrical signals produced by the electrodes, and producing output signals corresponding to the subject's eye movements; and
   means for displaying output signals produced by the signal processing means.

2. The apparatus according to claim 1, wherein the at least one visual cue is disposed inside the helmet within the visual field of the subject when the helmet is on the subject's head.

3. The apparatus according to claim 1, wherein the signal processing means and display means are disposed on the helmet.

4. The apparatus according to claim 1, wherein the signal processing means comprises:
   at least one amplifier for amplifying the electrical signals produced by the electrodes;
   an A/D converter for receiving the output from the amplifier and producing a digital signal therefrom; and
   logic circuitry for processing the digital signal, controlling illumination of the visual cue, and producing output signals corresponding to the subject's eye movements.

5. The apparatus according to claim 4, wherein the A/D converter is disposed on the helmet, and the logic circuitry and display means are separate from the helmet.

6. The apparatus according to claim 5, wherein the logic circuitry and display means comprise a personal computer.

7. The apparatus according to claim 1, further comprising at least one sound-emitting device disposed within the helmet, wherein the sound-emitting device is controlled by the signal processing means.

8. The apparatus according to claim 7, wherein two sound-emitting devices are disposed within the helmet, one adjacent each of the subject's ears when the helmet is on the subject's head.

9. The apparatus according to claim 7, wherein the sound-emitting device disposed within the helmet is a loudspeaker.

10. The apparatus according to claim 1, further comprising a power supply.

11. The apparatus according to claim 10, wherein the power supply is a battery.

12. The apparatus according to claim 1, wherein the at least one visual cue is at least three visual cues.

13. The apparatus according to claim 12, wherein the visual cues are disposed inside the helmet within the visual field of the subject when the helmet is on the subject's head, the visual cues being located at the center, left, and right of the subject's visual field.

14. The apparatus according to claim 13, wherein the visual cues at the left and right of the subject's visual field correspond to eye movements in the range of about 10 to about 25 degrees to the left or right, from center.

15. The apparatus according to claim 14, wherein the visual cues at the left and right of the subject's visual field correspond to eye movements in the range of about 12 to about 17 degrees to the left or right, from center.

16. A method for diagnosing a neurological disorder in a subject, comprising:
   (a) providing at least three visual cues within the subject's visual field while blocking any other visual stimuli from the subject's visual field, the visual cues capable of being switched from on to off states;
   (b) switching on the central visual cue;
   (c) switching off the central visual cue and switching on either one of the left or right visual cues;
   (d) switching off the left or right visual cue and switching on the central visual cue, wherein the subject is instructed to look at the central visual cue and then away from whichever of the left or right visual cues is subsequently switched on;
   (e) measuring the direction of eye movement in response to the switching on of either the left or right visual cue;
   (f) determining whether the subject's eye movements were as instructed;
   (g) repeating steps (b) to (f) a prescribed number of times; and
   (h) obtaining a score of the total number of correct or incorrect eye movements; wherein the score is diagnostic of the disorder and wherein an apparatus according to claim 12 is employed.

17. The method according to claim 16, wherein steps (b) to (f) are repeated 50 to 100 times.

18. The method according to claim 16, wherein an elapsed time between switching off the central visual cue and switching on either the left or right visual cue is between about 0.2 and 1.0 second.

19. The method according to claim 16, wherein an elapsed time between switching off the central visual cue and switching on either the left or right visual cue is randomized.

20. The method according to claim 16, wherein the switching on of either the left or the right visual cue is randomized.

21. The method according to claim 16, wherein the neurological disorder is associated with lack of attentiveness.

22. The method according to claim 21, wherein the neurological disorder is ADD.

23. The method according to claim 21, wherein the neurological disorder is ADHD.

24. A method for treating a neurological disorder in a subject, comprising:
   (a) providing visual cues within the left, right, and center of the subject's visual field while blocking any other visual stimuli from the subject's visual field, the visual cues capable of being switched from on to off states;
   (b) switching on the central visual cue;
   (c) switching off the central visual cue and switching on either one of the left or right visual cues;
   (d) switching off the left or right visual cue and switching on the central visual cue, wherein the subject is instructed to look at the central visual cue and then away from whichever of the left or right visual cues is subsequently switched on;
   (e) measuring the direction of eye movement in response to the switching on of either the left or right visual cue;

(f) determining whether the subject's eye movements were as instructed;

(g) providing positive reinforcement if the subject's eye movement was correct and/or negative reinforcement if the subject's eye movement was incorrect; and (h) repeating steps (b) to (f) a prescribed number of times.

25. The method according to claim 24, wherein steps (b) to (f) are repeated 50 to 100 times.

26. The method according to claim 24, wherein an elapsed time between switching off the central visual cue and switching on either the left or right visual cue is between about 0.2 and 1.0 second.

27. The method according to claim 24, wherein an elapsed time between switching off the central visual cue and switching on either the left or right visual cue is randomized.

28. The method according to claim 24, wherein the switching on of either the left or the right visual cue is randomized.

29. The method according to claim 24, where the neurological disorder is associated with a lack of attentiveness.

30. The method according to claim 29, wherein the neurological disorder is ADD.

31. The method according to claim 29, wherein the neurological disorder is ADHD.

32. The method according to claim 24, further comprising the step of obtaining a score of the total number of correct or incorrect eye movements, wherein reinforcement is provided depending on said score.

* * * * *